US007582431B2

(12) United States Patent
Drmanac et al.

(10) Patent No.: US 7,582,431 B2

(45) Date of Patent: Sep. 1, 2009

(54) ENHANCED SEQUENCING BY HYBRIDIZATION USING POOLS OF PROBES

(75) Inventors: Radoje Drmanac, Palo Alto, CA (US); Snezana Drmanac, Palo Alto, CA (US); David Kita, Foster City, CA (US); Cory Cooke, San Mateo, CA (US); Chongjun Xu, San Jose, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 435 days.

(21) Appl. No.: 10/987,549

(22) Filed: Nov. 12, 2004

(65) Prior Publication Data

US 2005/0191656 A1 Sep. 1, 2005

Related U.S. Application Data

(62) Division of application No. 09/479,608, filed on Jan. 6, 2000, now Pat. No. 6,864,052.

(60) Provisional application No. 60/115,284, filed on Jan. 6, 1999.

(51) Int. Cl.

| | |
|---|---|
| ***C12Q 1/68*** | (2006.01) |
| ***C07H 21/04*** | (2006.01) |
| ***C12P 19/34*** | (2006.01) |

(52) U.S. Cl. ....................... 435/6; 435/91.1; 435/91.52; 536/23.1; 536/24.32; 536/25.3

(58) Field of Classification Search ....................... None
See application file for complete search history.

(56) References Cited

U.S. PATENT DOCUMENTS

| | | | |
|---|---|---|---|
| 5,002,867 | A | 3/1991 | Macevicz |
| 5,202,231 | A | 4/1993 | Drmanac et al. |
| 5,525,464 | A | 6/1996 | Drmanac et al. |
| 5,744,305 | A | 4/1998 | Fodor et al. |
| 6,355,419 | B1 | 3/2002 | Alfenito |
| 6,537,755 | B1 | 3/2003 | Drmanac |

FOREIGN PATENT DOCUMENTS

| | | |
|---|---|---|
| WO | WO-95/09248 | 4/1995 |
| WO | WO-95/11995 | 5/1995 |
| WO | WO-96/17957 | 6/1996 |
| WO | WO-98/31836 | 7/1998 |
| WO | WO-99/09217 | 2/1999 |

OTHER PUBLICATIONS

Bains, Genomics, 11:294-301 (1991).
Bains et al., J. Theor. Biol., 135:303-307 (1988).
Drmanac et al., Genomics, 4:114-128(1989).
Drmanac et al., International Journal of Genomic Research, 1(1):59-79 (1992).
Drmanac et al., Scientia Yugoslavica, 16(1-2):97-107 (1990).
Khrapko et al., FEBS Lett., 256(1-2):118-122 (1989).

*Primary Examiner*—Lori A Clow
(74) *Attorney, Agent, or Firm*—Marshall, Gerstein & Borun LLP

(57) ABSTRACT

The invention provides methods for sequencing by hybridization (SBH) using pools of probes that allow greater efficiency in conducting SBH by reducing the number of separate measurements of hybridization signals required to identify each particular nucleotide in a target nucleic acid sequence. The invention also provides pools and sets of pools of probes, as well as methods of generating pools of probes.

6 Claims, 4 Drawing Sheets

ENHANCED SEQUENCING BY HYBRIDIZATION USING POOLS OF PROBES

This application is a divisional application of U.S. application Ser. No. 09/479,608 which was filed Jan. 6, 2000 now U.S. Pat. No. 6,864,052 and claimed benefit of priority of U.S. Provisional Application No. 60/115,284 filed Jan. 6, 1999. The entire disclosure of each of the foregoing applications is incorporated herein by reference.

FIELD OF THE INVENTION

This invention relates in general to methods and apparatus for nucleic acid sequence analysis, in particular sequence analysis using sequencing by hybridization.

BACKGROUND

The rate of determining the sequence of the four nucleotides in nucleic acid samples is a major technical obstacle for further advancement of molecular biology, medicine, and biotechnology. Nucleic acid sequencing methods which involve separation of nucleic acid molecules in a gel have been in use since 1978.

The traditional method of determining a sequence of nucleotides (i.e., the order of the A, G, C and T nucleotides in a sample) is performed by preparing a mixture of randomly-terminated, differentially labelled nucleic acid fragments by degradation at specific nucleotides, or by dideoxy chain termination of replicating strands. Resulting nucleic acid fragments in the range of 1 to 500 bp are then separated on a gel to produce a ladder of bands wherein the adjacent samples differ in length by one nucleotide.

The present invention relates to an alternative methodology for sequencing a target nucleic acid known as sequencing by hybridization (SBH). The array-based approach of SBH does not require single base resolution in separation, degradation, synthesis or imaging of a nucleic acid molecule. Using mismatch discriminative hybridization of short oligonucleotides K nucleotides in length, lists of constituent k-mer oligonucleotides may be determined for target nucleic acid. Sequence for the target nucleic acid may be assembled by uniquely overlapping scored oligonucleotides.

Nucleic acid sequencing by hybridization shares interesting parallels with conducting a computer search of a text file for a particular word or a phrase. In each case, a large string of characters is probed with a specific shorter string to detect matching sequences. In a computer text search, the search string or strings (key words) are used to browse a large Internet or local data base to identify the subset of specific documents containing perfect sequence matches, which is then retrieved for further review or analysis. In SBH, oligonucleotide probes ranging from 4 to 25 characters in length are used to browse libraries of nucleic acid segments to identify nucleic acid molecules containing exact complementary sequences. These molecules may then be further analyzed by mapping or clustering, or by partial or full sequencing.

In the case of a hybridization search of four simple DNA samples with four different 5-mer probes (which could be called key words, or strings), each sample binds a different combination of probes, leading to a characteristic hybridization pattern. Each positive binding (or hybridization) event in a given DNA sample provides a discrete piece of information about its sequence. Neither the frequency nor location of the string within the DNA molecule is obtained from a hybridization search, as is also the case in most computer text searches. For example, a positive search result for the word "tag" in a set of document titles does not identify whether the word is positioned at the beginning, middle, or end of the selected titles, nor whether it occurs once, twice, or many times in any of these titles. Similarly, the entire DNA is sampled by random probe-binding trials, without determination of exactly where in the chain particular probes bind.

In a computer search of English language text, the complexity of the English alphabet (26 letters) generally allows a meaningful search of a given text to be done with one or a few specific words. With a DNA search, the simple four-letter genetic alphabet requires use of either more or longer "words" (strings) to precisely identify a specific DNA. A simple word like "cat" might yield useful results in a computer search of the Internet, but the genetic triplet "CAT" occurs far too frequently (about once in every sixty-four triplets) to be of much use in DNA identification. The lengths of the DNA string (sequence) and the probe (interrogating string) are important parameters in devising a successful SBH experiment. By choosing appropriate probe and sample lengths, a researcher can obtain useful sequence data.

The first potential probe binding site in a nucleotide sequence chain starts at the first base and extends for the length of the probe. The second probe binding site starts at the second base and overlaps the first probe binding site, less one base. This means that if a complete (or sufficient) set of probes is tested, the end of each positive probe overlaps with the beginning of another positive probe, except in the case of the last positive probe in the target. In each sequence assembly cycle, four potential overlap probes are checked. Starting with a positive probe AAATC, the next positive overlapping probe to the right may be AATCA, AATCC, AATCG or AATCT. Of these probes, only AATCG is found to be positive and is used for further assembly. The cycles are repeated in both directions until all positive probes are incorporated and the complete sequence is assembled. By extension, the same process applies to a longer target nucleic acid if enough probes of appropriate length are used to identify uniquely overlapped strings within it.

The use of overlapping positive probes is a key aspect of SBH methods. This "overlap principle" allows the identification of sequences within a target DNA that are longer than any of the probes used in the assembly process. Probe overlap allows indirect assignment of one out of four bases for each position in the analyzed DNA chain without performing any actual positional measurements on the sample. The base/position information is in fact derived from the known sequences of the oligonucleotide probes obtained by accurate chemical synthesis.

Thus, a DNA hybridization search is effectively a highly parallel molecular computation process with fully random access to the "input data," in this case a polynucleotide chain that may be thousands of bases long. These fundamental characteristics of the SBH process confer unique opportunities for miniaturization and parallel analyses, leading to speed and cost efficiencies not available with other sequencing methods.

Because the sequences of DNA molecules are non-random and irregular, statistical artifacts arise that must be addressed in SBH experiments. Even when the lengths of DNA targets and probes are selected to achieve a statistical expectation that each probe sequence occurs no more than once in the target, so-called "branching ambiguities" can occur. (Drmanac et al., Yugoslav Patent Application 570/87 (1987) issued as U.S. Pat. No. 5,202,231 (1993); Drmanac et al., "Sequencing of Megabase Plus DNA by Hybridization: Theory of the Method," *Genomics,* 4:114-128 (1989).) Take the case of three probes that positively hybridize to a target DNA: TAGA, AGAC and AGAT. Both the second and the third probes overlap with the first probe, sharing the bases AGA and giving extended sequences TAGAC and TAGAT, respectively. Due to the occurrence of the sequence AGA in both the second and third probes (e.g. due to double AGA occurrence in the target), there is not enough information available to decide which of the two probes is actually the one that overlaps with the first probe in the sample. Sequence assembly can thus proceed along either of the two branches, only one of which may be correct. Branching ambiguities may be resolved if a reference sequence for the target is known.

By using all possible probes of a given length, a researcher can unambiguously determine a target nucleotide sequence, provided the target nucleic acid is short enough that most overlap sequences occur no more than once. The only other exception to this rule is tandem repeat regions (e.g.: AAAAAAAAAA(SEQ ID NO:1), ACACACACAC(SEQ ID NO:2)) that are longer than the probe length. In such cases, the exact length of these repeats may be determined by use of a special subset of longer probes. Longer targets may require longer probes for unambiguous sequence determination. A variety of ways have been proposed to increase the read length with a given set of probes, or to reduce the number of experimental probe/target scores needed to sequence a target nucleic acid. These include the use of redundant combinations of probes, competitive hybridization and overlapped clones (Drmanac et al., Yugoslav Patent Application 570/87 (1987) issued as U.S. Pat. No. 5,202,231 (1993); Drmanac et al., "Sequencing of Megabase Plus DNA by Hybridization: Theory of the Method," *Genomics,* 4:114-128 (1989)), gapped probes (Bains et al., "A Novel Method for Nucleic Acid Sequencing," *J. Theor. Biol.,* 135:303-307 (1988)) and binary probes (Pevzner et al., "Towards DNA Sequencing Chips," *Mathematical Foundations of Computer Science* 1994 (Eds. I. Privara, B. Rovan, P. Ruzicka,) pp. 143-158, The Proceedings of 19th International Symposium, MFCS '94, Kosice, Slovakia, Springer-Verlag, Berlin (1995)), continuous stacking hybridization (Khrapko et al., "An Oligonucleotide Hybridization Approach to DNA Sequencing," *FEBS Letters,* 256:118-122 (1989), and the simultaneous sequencing of similar genomes (Drnanac et al., "Sequencing by Hybridization (SBH) With Oligonucleotide Probes as an Integral Approach for the Analysis of Complex Genomes," *International Journal of Genomic Research,* 1(1): 59-79 (1992).

There are several approaches available to achieve sequencing by hybridization. In a process called SBH Format 1, nucleic acid samples are arrayed, and labeled probes are hybridized with the samples. Replica membranes with the same sets of sample nucleic acids may be used for parallel scoring of several probes and/or probes may be multiplexed (i.e., probes containing different labels). Nucleic acid samples may be arrayed and hybridized on nylon membranes or other suitable supports. Each membrane array may be reused many times. Format 1 is especially efficient for batch processing large numbers of samples.

In SBH Format 2, probes are arrayed at locations on a substrate which correspond to their respective sequences, and a labelled nucleic acid sample fragment is hybridized to the arrayed probes. In this case, sequence information about a fragment may be determined in a simultaneous hybridization reaction with all of the arrayed probes. For-sequencing other nucleic acid fragments, the same oligonucleotide array may be reused. The arrays may be produced by spotting or by in situ synthesis of probes.

In Format 3 SBH, two sets of probes are used. In one embodiment, a set may be in the form of arrays of probes with known positions in the array, and another, labelled set may be stored in multiwell plates. In this case, target nucleic acid need not be labelled. Target nucleic acid and one or more labelled probes are added to the arrayed sets of probes. If one attached probe and one labelled probe both hybridize contiguously on the target nucleic acid, they can be covalently ligated, producing a detected sequence equal to the sum of the length of the ligated probes. The process allows for sequencing long nucleic acid fragments, e.g. a complete bacterial genome, without nucleic acid subcloning in smaller pieces.

However, to sequence long nucleic acids unambiguously, SBH involves the use of long probes. As the length of the probes increases, so does the number of probes required to generate sequence information. Each 2-fold increase in length of the target requires a one-nucleotide increase in the length of the probe, resulting in a four-fold increase in the number of probes required (the complete set of probes of length K contains $4^k$ probes). For example, de novo sequencing without additional mapping information of 100 nucleotides of DNA requires 16,384 7-mers; sequencing 200 nucleotides requires 65,536 8-mers; 400 nucleotides, 262,144 9-mers; 800 nucleotides, 1,048,576 10-mers; 1600 nucleotides, 4,194,304 11-mers; 3200 nucleotides, 16,777,216 12-mers; 6400 nucleotides, 67,108,864 13-mers; and 12,800 nucleotides requires 268,435,456 14-mers.

From any given sequence, however, most of the probes will be negative, and thus much of the information is redundant. For sequencing a 200 bp target nucleic acid with 65,536 8-mers, for example, about 330 measurements (positive and negative) are made for each base pair (65,536 probe measurements/200 bp). For sequencing a 6400 bp sequence with 67,108,864 13-mer probes, the measurement redundancy increases to about 10,500. An improvement in SBH that increases the efficiency and reduces the number of necessary measurements would greatly enhance the practical ability to sequence long pieces of DNA de novo. Such an improvement would, of course, also enhance resequencing and other applications of SBH.

Of interest are disclosures of the use of "binary" pools [see Pevzner and Lipschutz, in Mathematical Foundations of Computer Science 1994, Springer-Verlag, Berlin, pages 143-158 (1995?)], "alternating" probes [Pevzner and Lipschutz, supra], "gapped" probes [Pevzner and Lipschutz, supra; Bains and Smith, J. Theor. Biol., 135:303-307 (1988)], redundant combinations (pools) of probes [Drmanac et al., U.S. Pat. No.5,202,231], probes with degenerate ends in SBH [Bains, Genomics, 11:294-301 (1991)]. See also pools of multiplexed probes [Drmanac and Crkvenjakov, Scientia Yugoslavica, 16(1-2):97-107 (1990)].

Also of interest is the suggestion in WO 95/09248 suggests that extension of the sequence of probe X may be carried out by comparing signals of (a) the four possible overlapping probes generated by a one base extension of the sequence of X and (b) the three single mismatch probes wherein the mismatch position is the first position of X, and adding a base extension only if probe X and the probe created by the base extension have a significantly positive signal compared to the other six probes.

SUMMARY OF THE INVENTION

Figure 1:
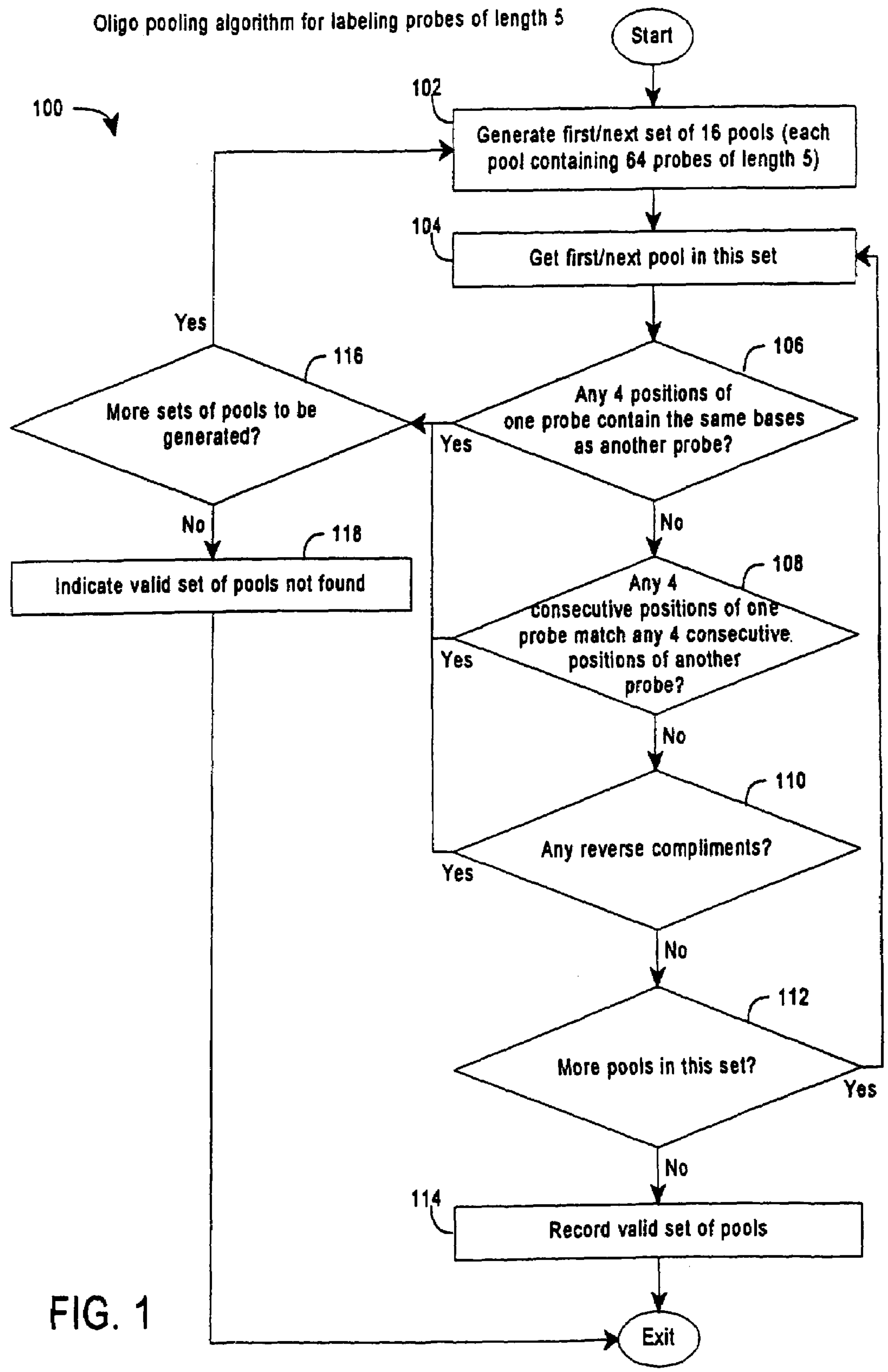
FIG. 1 shows a flow chart for an algorithm to generate pools of probes.

The present invention enhances SBH methods by providing methods and pools of probes that allow greater efficiency in conducting SBH. The use of pools of probes allows a great reduction in the level of redundancy (R), i.e., the number of separate measurements of hybridization signals, required to identify each particular nucleotide in a target nucleic acid sequence.

The present invention also provides pools and sets of pools of probes, as well as methods of synthesizing pools of probes. In such a method of synthesizing an pool of probes, maximal randomization of the probes within a pool is achieved if not more than two different bases are incorporated at one position, and/or if all 6 possible base mixes (A+T, A+C, A+G, T+C, T+G, C+G) are used equally in the synthesis.

The present invention also provides improved SBH sequence assembly methods involving, e.g., the use of an initial filtering algorithm to remove probes that fail to overlap with a prespecified number of other probes, the use of rescoring to better discriminate true positive probes from false positive probes, e.g., by taking into account scores of probes containing a single or double mismatch, the use of continuous value scores for all probes in sequence assembly rather than scoring probes as positive/negative wherein an overlapping sequence comprising 3 or more probes is scored for probability of correctness based on scores of its constituent probes, the use of statistical analysis of scores or probabilities of the probes within an assembled sequence to determine the likelihood that an assembled sequence is the correct target sequence, and the use of likelihoods or other probability scores to determine whether a mutation exists in a reference sequence.

The invention provides methods of identifying one or more sequences of a target nucleic acid comprising: a)contacting a target nucleic acid with a first set of pools of probes, wherein at least one pool in the set comprises a mixture of two or more probes having different sequences in information regions of the probes, under conditions which produce, on average, more probe:target hybridization with probes which are perfectly complementary to the target nucleic acid in the information region of the probes than with probes which are mismatched in the information regions; b) detecting a first subset of pools for which a level of hybridization indicates that there is at least one perfectly complementary probe within each pool; and c) identifying one or more sequences of the target nucleic acid from the first subset of pools detected in step (b) by compiling overlapping sequences of the information regions of the probes in the subset of detected pools, wherein one or more pooling false positive probes are eliminated as a result of compilation of overlapping sequences. In one aspect, the method, further comprises, following step (b) and before step (c), the steps of: a) contacting the target nucleic acid with a second set of pools of probes containing at least one probe having the same information region as a probe in the first set, b) detecting a second subset of pools for which the level of hybridization indicates that there is at least one perfectly complementary probe within each pool; and c) eliminating probes with the same information regions present in both the first set of pools of probes and the second set of pools of probes that are not present in both the first detected subset of pools and the second detected subset of pools. In one aspect, the first and second sets of pools of probes comprise the same information regions. In another aspect, the first and second sets of pools of probes comprise the same probes.

The invention also provides methods of identifying one or more sequences of a target nucleic acid comprising: a) contacting a target nucleic acid with a first set of pools of probes, wherein at least one pool in the set comprises a mixture of two or more probes having different sequences in information regions of the probes, under conditions which produce, on average, more probe:target hybridization with probes which are perfectly complementary to the target nucleic acid in the information region of the probes than with probes which are mismatched in the information regions; b) assigning a hybridization score to each probe wherein each probe within a pool is assigned the same hybridization score, and c) identifying one or more sequences of the target nucleic acid by analysis of hybridization scores of overlapping probes, wherein one or more probes with false high scores arising from pooling of probes are eliminated by analysis of hybridization scores of overlapping. In one aspect a statistical analysis of hybridization scores is performed in step (c). In another aspect of the method, step (c) further comprises calculating a score for the identified one or more sequences of the target nucleic acid.

In another embodiment, the method further comprises, after step (b) and before step (c), the steps of: a) contacting the target nucleic acid with a second set of pools of probes containing at least one probe having the same information region as a probe in the first set, b) assigning a hybridization score to each probe wherein each probe within a pool is assigned the same hybridization score. In addition, the invention provides a method further comprising the step of c) eliminating the higher of two scores for probes present in both the first set and second set of pools of probes. In one aspect of the invention, the first and second sets of pools of probes comprise the same information regions, and in another aspect, the first and second sets of pools of probes comprise the same probes.

Methods of the invention include those wherein the target nucleic acid is labeled and those wherein the probes are labeled. In one aspect, the label is a fluorophore.

In another aspect, the label is attached to a terminal nucleotide and or to an internal nucleotide. Methods include those wherein the set of pools of probes is immobilized on one or more solid supports, and those wherein the pools of probes are arranged in a spatially-addressable array in which each pool has a unique address. In other aspects, methods are provided wherein the target nucleic acid is immobilized on one or more solid supports.

The invention further provides methods of identifying one or more sequences of a target nucleic acid comprising: a) contacting a target nucleic acid with a first set of pools of immobilized probes and a first set of pools of labeled probes, wherein at least one pool in either the first set of pools of immobilized probes or the first set of pools of labeled probes, or both, comprises a mixture of two or more probes having different sequences in the information regions of the probes, under conditions which produce, on average, more probe: target hybridization for probes which are perfectly complementary to the target nucleic acid in the information region than with probes which are mismatched in the information region; b) covalently joining adjacently hybridized immobilized probes and labeled probes to provide a first set of covalently joined probes; c) detecting a first subset of pools of covalently joined probes for which a level of hybridization indicates that there is at least one perfectly complementary covalently joined probe within each pool; and d) identifying one or more sequences of the target nucleic acid from the first subset of covalently joined pools or probes detected in step (c) by compiling overlapping sequences of the information regions of covalently joined probes in the subset of detected pools, wherein one or more covalently joined pooling false positive probes are eliminated as a result of compilation of overlapping sequences.

In another embodiment, the method further comprising, following step (c) and before step (d), the steps of: a) contacting the target nucleic acid with a second set of pools of immobilized probes and a second set of pools of labeled probes, wherein at least one probe in the second set of immobilized probes has the same information region as a probe in the first set of pools of immobilized probes, or at least one probe in the second set of labeled probes has the same information region as a probe in the first set of pools of labeled probes, b) covalently joining adjacently hybridized immobilized probes and labeled probes to provide a second set of covalently joined probes; c) detecting a second subset of covalently joined pools or probes for which a level of hybridization indicates that there is at least one perfectly complementary probe within each pool; and d) eliminating covalently joined probes with the same information regions present in both the first subset of covalently joined pools of probes and the second subset of covalently joined pools of probes that are not present in both the first detected subset of covalently joined pools of probes and the second detected subset of covalently joined pools of probes.

The invention also provides methods of identifying one or more sequences of a target nucleic acid comprising: a) contacting a target nucleic acid with a first set of pools of immobilized probes and a first set of pools of labeled probes, wherein at least one pool in the first set of pools of immobilized probes or at least one pool in the first set of pools of labeled probes or both, comprises a mixture of two or more probes having different sequences in the information regions of the probes, under conditions which produce, on average, more probe:target hybridization for probes which are perfectly complementary to the target nucleic acid in the information region than with probes which are mismatched in the information region; b) covalently joining adjacently hybridized immobilized probes and labeled probes to provide a first set of covalently joined probes; c) assigning a hybridization score to each covalently joined probe in the first set of covalently joined probes wherein each probe within a pool is assigned the same hybridization score, and d) identifying one or more sequences of the target nucleic acid from overlapping covalently joined probes by analysis of hybridization scores of overlapping covalently joined probes wherein one or more covalently joined probes with false high scores arising from pooling of probes are eliminated by analysis of hybridization scores of overlapping probes. In one aspect, the method of the invention further comprises after step (c) and before step (d) the steps of a) contacting the target nucleic acid with a second set of pools of immobilized probes and a second set of pools of labeled probes, wherein at least one probe in the second set of immobilized probes has the same information region as a probe in the first set of pools of immobilized probes, at least one probe in the second set of labeled probes has the same information region as a probe in the first set of pools of labeled probes, b) covalently joining adjacently hybridized immobilized probes and labeled probes to provide a second set of covalently joined probes; c) assigning a hybridization score to each covalently joined probe of the second set wherein each probe within a pool of covalently joined probes is assigned the same hybridization score. In still another aspect, the invention further comprises the step of d) eliminating the higher of two scores for covalently joined probes present in both the first set and second set of covalently joined pools of probes.

The invention provides methods wherein the first and second sets of pools of immobilized probes or sets of pools of labeled probes or both comprise the same information regions, as well as methods wherein the first and second sets of pools of immobilized probes or sets of pools of labeled probes or both comprise the same probes.

The invention provides methods where probes are labeled with a fluorophore, as well as methods wherein a label of the labeled probe is attached to a terminal nucleotide and/or attached to an internal nucleotide. Methods are provided wherein the set of pools of immobilized probes is immobilized on one or more solid supports, an/or the sets of pools of immobilized probes are arranged in a spatially-addressable array in which each pool has a unique address.

The invention further provides methods wherein a statistical analysis of hybridization scores is performed, as well as methods a step comprising calculating a score for the identified one or more sequences of the target nucleic acid The invention also provides methods wherein the pools of immobilized probes each consist of one probe, as well as methods wherein the pools of labeled probes each consist of one probe.

The invention also provides methods of sequencing a target nucleic acid, or determining the putative presence of a nucleotide sequence in a target nucleic acid, comprising the steps of: (a) contacting a target nucleic acid with a set of pools of probes wherein each pool comprises a mixed plurality of different probes (preferably of predetermined length and predetermined sequence), wherein the nucleotide sequences of at least two different probes in the pool differ within their information region, under conditions which discriminate in most cases between probe:target hybrids which are perfectly complementary in the information region of the probe and probe:target hybrids which are mismatched in the information region of the probe; (b) detecting those pools of probes of the set of pools of probes which hybridize with the target nucleic acid; and (c) determining the sequence of the target nucleic acid from the subset of pools detected in step (b) by compiling the overlapping sequences of the information regions of the probes in the detected pools, wherein pooling false positives are eliminated as a result of compilation of overlapping sequences.

The pooling methods of the invention may be applied to either Format 1, 2 or 3 SBH. Thus, the probes may be labeled or the target nucleic acid may be labeled. Labels may be fluorophores and may be attached to a terminal nucleotide or an internal nucleotide. Either the probes or the target nucleic acids may be immobilized on a solid support and/or arranged in a spatially-addressable array. In Format 1, the probes are labeled and the target nucleic acid(s) is(are) immobilized on a solid support. In Format 2, the target nucleic acid is labeled and the probes are immobilized on a solid support. In Format 3, some probes are immobilized and some probes are labeled, and either immobilized probes or labeled probes (in solution), or both, may be arranged in subpools. When both immobilized and labeled probes are pooled, the combination of immobilized and labeled probe subpools makes up a pool. For example, a Format 3 pooling method in which both the immobilized and the labeled probes are pooled may comprise the steps of: (a) contacting a target nucleic acid with a set of subpools of probes, wherein each probe is immobilized on a solid support, wherein the subpool comprises a mixed plurality of different probes (preferably of predetermined length and predetermined sequence), and wherein the nucleotide sequences of at least two different probes in the pool differ within their information region, under conditions which discriminate in most cases between probe:target hybrids which are perfectly complementary in the information region and probe:target hybrids which are mismatched in the information region; (b) contacting the array and target nucleic acid with a subpool of labeled probes (preferably of predetermined length and predetermined sequence) under conditions which discriminate between perfectly complementary labeled probe:target complexes and mismatched labeled probe:target complexes; (c) covalently joining adjacently hybridized immobilized probes and labeled probes; (d) identifying which pools of subpools of probes hybridized to the target nucleic acid; and (e) determining the sequence of the target nucleic acid by overlapping the sequences of the region of probes in the detected pools that hybridized, wherein false positives due to pooling are eliminated as a result of compilation of overlapping sequences.

Alternatively, only the labeled probes in solution may be pooled, while each immobilized probe has a unique address in a spatially addressable array. In another embodiment, only the immobilized probes may be pooled, and each pool may be associated with a unique address in a spatially addressable array.

The invention further provides a set of pools of probes wherein each probe comprises an information region, wherein said set of probes is sufficient to determine the sequence of an unknown target nucleic acid by overlapping sequences of the information region of two or more probes, and wherein at least one pool comprises two or more probes having different sequences in the information regions and having the same label or no label, and wherein the set of the pools of probes also satisfies one or more of the following rules describing the information regions of the probes, said rules selected from the group consisting of: (a) a consensus sequence of at least one pool in the set consists only of the letters selected from the group consisting of V, H, D, B, and N as defined in Table A below; (b) a consensus sequence of probes in each pool in the set comprises more than three different letters selected from the group consisting of A, C, G, T, U, M, R, W, S, Y, K, V, H, D, B, and N as defined in Table A below; (c) consensus sequences from each informative position of all pools in the set comprise more than eight letters selected from the group consisting of A, C, G, T, U, M, R, W, S, Y, K, V, H, D, B, and N as defined in Table A below; and (d) consensus sequences from each information region of all pools in the set comprise more than five different letters selected from the group consisting of A, C, G, T, U, M, R, W, S, Y, K, V, H, D, B, and N and at least one of the five letters is selected from the group consisting of M, R, W, S, Y, and K as defined in Table A below. A consensus sequence is determined by alignment of bases in probes within or among pools limiting degeneracy at each aligned position to either one, two, three or four possible bases at that position. Letter coding for all levels of degeneracy are shown in Table A. Alternatively, rules for the set may be selected from the group consisting of (a) no two probes of length K within the pool overlap by K-1 bases; (b) no two probes pools within a pool are reverse complements; (c) less than 50% of the probes in the set are repeated in any two pools within the set; (d) when two or more probes in a pool vary at a nucleotide position, there are no more than three different bases at that varied position; (e)no two probes in a pool overlap by a significant number of bases; and (e) there exists at least one nucleotide position wherein all probes within the pool are identical.

In one aspect, the set of pools of probes of the invention comprises all possible probes of the same length K, where K is greater than 3. In another aspect, each pool comprises more than 16 different probes or at least 32 different probes. In another aspect, the pools are arranged in a spatially-addressable array, and wherein each pool has an address. In still another aspect, at least two pools are mixed, wherein any two pools that are mixed are associated with different labels, and wherein all probes in a single pool are associated with the same label.

TABLE A

| Letter | Definition |
|---|---|
| A | A |
| C | C |
| G | G |
| T | T |
| U | U |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N | A or C or G or T/U |

DETAILED DESCRIPTION OF THE INVENTION

The present invention provides an improvement on the basic SBH method. According to the present invention, pools of probes are used to reduce the redundancy normally found in SBH protocols and to reduce the number of hybridization reactions needed to determine a target DNA sequence unambiguously.

For SBH of nucleic acids that are 1000-3200 bases in length, progressively more probes (from about 16,000 7-mers to 16 million 12-mers) must be scored. The present invention provides improved probe pooling and sequence assembly strategies that may significantly reduce the number of independent probe synthesis reactions, hybridization reactions, probe array size and readout time by about 10- to over 1000-fold. The invention is based on the discovery that when pools of unexpectedly large numbers of probes with diverse (dissimilar) sequences are hybridized with the target nucleic acid, and all probes in a pool are scored as positive if any one probe in the pool is positive, assembly of incorrect sequence is unlikely (i.e., the resulting assembled sequence will most likely be the correct target nucleic acid sequence) despite the co-scoring of negative probes in the pool as positive.

False positives due to experimental error (defined as "experimental false positives" herein) are observed with conventional SBH, and may be as high as 2-3% of all probes. Such experimental false positives maybe due to errors in probe synthesis (for example, the probe fixed to a spot on an array may have an erroneous nucleotide sequence), errors in hybridization or errors in scoring (for example, probes that are not full match probes may be erroneously scored as positive, due to unusually strong hybridization signals from single mismatch probes; unusually weak hybridization signals from full match probes, problems in setting the threshold of positive/negative scores, or errors in reading data).

In the methods of the present invention, the assignment of the same hybridization score to all probes in a pool (which in positive pools results in co-scoring of negative probes as positive) intentionally introduces additional false positives due to the pooling of probes, called "pooling false positives" herein. When positive/negative scoring is used in de novo sequencing, the total fraction of positive probes (Fp=number of positive probes/number of all probes), which includes true positives, experimental false positives and pooling false positives, can be no more than 25%, and is preferably 20% or less, and more preferably 10% or less.

According to one embodiment, all probes from a positive informational pool are initially scored as positive, and pooling false positives (as well as experimental false positives) are rejected as a result of their failure to overlap with other positive probe sequences in the same or in other positive pools. In comparison, prior strategies that used redundant or binary pools of probes (with different informational content) contemplated an identification of the true positive probes in the pool before overlapping the sequences of the positive probes.

The use of pools reduces dramatically the need for independent probe scoring, especially for longer probes needed for de novo sequencing of kb range targets. Also, a very small number of a few thousand scores may be sufficient to determine the sequence of a target nucleic acid only a few hundred bases in length. The use of pools is applicable to all SBH formats, including a format wherein pools of labeled probes are hybridized to immobilized target samples (Format 1 SBH), a format wherein labeled target is hybridized to immobilized pools of probes (e.g., one pool per spot, Format 2 SBH), and a format that utilizes both arrayed probes and labeled probes in solution (Format 3 SBH). Several options are available in Format 3 SBH; the immobilized probes can be pooled, or the labeled probes can be pooled, or both immobilized and labeled probes can be pooled.

Pools are demonstrated herein to allow sequence assembly with a minimal number of experimental hybridization scores. However, pools provide additional challenges for potential optimization of sensitivity and specificity, such as the ability to detect the positive signal of one out of thousands of labeled probes hybridized together in one pool, and the ability to discriminate negative pools having a cumulative hybridization signal that may be close to the strength of a positive signal, based on hybridization of several single mismatch probes and one end-mismatch probe to the target nucleic acid (while keeping the fraction of pools with a positive signal to an Fp=⅕).

a. Definitions

"Probes" refers to relatively short pieces of nucleic acids, preferably DNA. Probes are preferably shorter than the target DNA by at least one nucleotide, and more preferably they are of a length commonly referred to as oligonucleotides, that is they are 25 nucleotides or fewer in length, still more preferably 20 nucleotides or fewer in length. Of course, the optimal length of a probe will depend on the length of the target nucleic acid being analyzed, and the availability of additional reference sequence or mapping information. For de novo sequencing, without additional mapping information, of a target nucleic acid composed of about 100 or fewer nucleotides, the probes are at least 7-mers; for a target of about 100-200 nucleotides, the probes are at least 8-mers; for a target nucleic acid of about 200-400 nucleotides, the probes are at least 9-mers; for a target nucleic acid of about 400-800 nucleotides, the probes are at least 10-mers; for a target nucleic acid of about 800-1600 nucleotides, the probes are at least 11-mers; for a target of about 1600-3200 nucleotides, the probes are at least 12-mers, for a target of about 3200-6400 nucleotides, the probes are at least 13-mers; and for a target of about 6400-12,800 nucleotides, the probes are at least 14-mers. For every additional two-fold increase in the length of the target nucleic acid, the optimal probe length is one additional nucleotide.

Those of skill in the art will recognize that for Format 3 SBH applications, the above-delineated probe lengths are post-ligation and/or post-extension as described herein. Thus, as used throughout, specific probe lengths refer to the actual length of the probes for format 1 and 2 SBH applications and the lengths of ligated probes in Format 3 SBH. When probes are extended by one base using DNA polymerase to incorporate differentially labeled dideoxynucleotides (thereby allowing identification of the single incorporated base by detecting the label), the probe length would refer to the length post-extension.

Probes are normally single stranded, although double-stranded probes may be used in some applications. While typically the probes will be composed of naturally-occurring bases and native phosphodiester backbones, they need not be. For example, the probes may be composed of one or more modified bases, such as 7-deazaguanosine, or one or more modified backbone interlinkages, such as a phosphorothioate. The only requirement is that the probes be able to hybridize to the target nucleic acid. A wide variety of modified bases and backbone interlinkages that can be used in conjunction with the present invention are known, and will be apparent to those of skill in the art.

The length of the probes described above and throughout the specification refers to the length of the informational content (i.e., the information region or the informative region) of the probes, not necessarily the actual physical length of the probes. The probes used in SBH frequently contain degenerate ends that do not contribute to the information content of the probes. For example, SBH applications frequently use mixtures of probes of the formula $N_xB_yN_z$, wherein N represents any of the four nucleotides and varies for the polynucleotides in a given mixture, B represents any of the four nucleotides but is the same for each of the polynucleotides in a given mixture, and x, y, and z are all integers. Preferably, x is an integer between 0 and 5, y is an integer between 4 and 20, and z is an integer between 0 and 5. Hybridization discrimination of mismatches in these degenerate probe mixtures refers only to the length of the informational content, not the full physical length.

"Target Nucleic Acid" refers to the nucleic acid of interest, typically the nucleic acid that is sequenced in the SBH assay. The nucleic acid can be any number of nucleotides in length, depending on the length of the probes, but is typically on the order of 100, 200, 400, 800, 1600, 3200, 6400, or even more nucleotides in length. The target nucleic acid may be composed of ribonucleotides, deoxyribonucleotides or mixtures thereof. Typically, the target nucleic acid is a DNA. While the target nucleic acid can be double-stranded, it is preferably single stranded so that hybridization to the probe can occur. Moreover, the target nucleic acid can be obtained from virtually any source. Depending on the length of the source nucleic acid, it is preferably fragmented to form smaller targets prior to use in an SBH assay. Like the probes, the target nucleic acid can be composed of one or more modified bases or backbone interlinkages.

Nucleotide bases "match" or are "complementary" if they form a stable duplex by hydrogen bonding under specified conditions. For example. under conditions commonly employed in hybridization assays, adenine ("A") matches thymine ("T"), but not guanine ("G") or cytosine ("C"). Similarly, G matches C, but not A or T. Other bases which will hydrogen bond in less specific fashion, such as inosine or the Universal Base ("M" base, Nichols et al 1994), or other modified bases, such as methylated bases, for example, are complementary to those bases with which they form a stable duplex under specified conditions. A probe is said to be "perfectly complementary" or is said to be a "perfect match" if each base in the probe forms a duplex by hydrogen bonding to a base in the target nucleic acid according to the Watson and Crick base pairing rules (i.e., absent any surrounding sequence effects, the duplex formed has the maximal binding energy for a particular probe). "Perfectly complementary" and "perfect match" are also meant to encompass probes which have analogs or modified nucleotides. A "perfect match" for an analog or modified nucleotide is judged according to a "perfect match rule" selected for that analog or modified nucleotide (e.g., the binding pair that has maximal binding energy for a particular analog or modified nucleotide). Each base in a probe that does not form a binding pair according to the "rules" is said to be a "mismatch" under the specified hybridization conditions.

"Pools of probes" (or informative pools of probes) refers to pools of probes selected for their information content. Preferably, individual pools of probes comprise probes in which the information content (i.e., the sequence of the information region) differs in more than one position. Preferably, individual pools comprise probes that do not overlap over significant portions of their length (for example, an individual pool should not contain the probes AGGATCT and GGATCTG, because the two probes overlap with a one-nucleotide overhang). The probes in an pool need not all be of the same length.

A "set of pools" refers to a set of probes that is sufficient to identify or determine the sequence of a target nucleic acid by SBH, wherein the probes are grouped into pools. The content of the set will vary depending on the length of probes, the length of the target nucleic acid, and the type of sequencing application (e.g., de novo sequencing, resequencing, detection of POLYMORPHISMS, diagnostic sequencing, forensic uses, etc.). For de novo sequencing, the set may be a set of all possible probes of length K but may alternatively be a subset thereof. For example, a set of all possible probes of length K can be reduced by 50% if reverse complements are eliminated. A universal set of probes includes sufficient probes to analyze a DNA fragment with prespecified precision, e.g. with respect to the redundancy of reading each base pair ("bp"). These sets may include more probes than are necessary for one specific fragment, but may include fewer probes than are necessary for testing thousands of DNA samples of different sequence with sequence-specific probes. In addition, some pools in the set may have only one probe.

b. Preparation of Probes

Probes may be prepared and optionally labeled as described in Int'l Publication No. WO 98/31836 published Jul. 23, 1998 and WO 99/09217 published Feb. 28, 1999, both of which are incorporated herein by reference. See, e.g., Examples 1 through 4, 15 of WO 98/31836. Oligonucleotide probes may incorporate modified bases and may be labeled with fluorescent dyes, chemiluminescent systems, radioactive labels (e.g., $^{35}S$, $^{3}H$, $^{32}P$ or $^{33}P$), non-radioactive isotopes, isotopes detectable by mass spectrometry (e.g., electrophore mass labels (EMLs), ligands which can serve as specific binding partners to a labeled antibody, enzymes, antibodies which can serve as a specific binding partner for a labeled ligand, antigens, groups with specific reactivity, and electrochemically detectable moieties.

The probes may optionally be disposed on a solid substrate (e.g., on arrays, particles or other solid supports) as described in Int'l Publication No. WO 98/31836 published Jul. 23 1998 and WO 99/09217 published Feb. 28, 1999, both of which are incorporated herein by reference. See, e.g:, Examples 5 through 6, 15, and 32 of WO 98/31836. See also, e.g., Examples 33 through 36 of WO 99/09217. Probes may be fixed to a support (i.e., "fixed probes" or "immobilized probes") by a number of methods known to those skilled in the art, including by passive adsorption, by covalent binding (e.g., by formation of amide groups or phosphodiester linkage between the probe and the support), and by strong binding interactions such as biotin-streptavidin interaction (e.g., through immobilization of biotinylated probes on streptavidin-coated supports). For example, glass, polystyrene, Teflon, nylon, silicon or fluorocarbon supports may be used.

A variety of techniques have been described for synthesizing and/or immobilizing arrays of polynucleotides, including in situ synthesis, where the polynucleotides are synthesized directly on the surface of the substrate (see, e.g., U.S. Pat. No.5,744,305 to Fodor, et al.,) and attachment of pre-synthesized polynucleotides to the surface of a substrate at discrete locations (see, e.g., WO 98/31836, incorporated herein by reference). Additional methods are described in WO 98/31836, incorporated herein by reference, at pages 41-45 and 47-48, among other places, and in the references cited therein. The present invention is suitable for use with any of these currently available, or later developed, techniques. Additionally, methods for normalizing different quantities of compounds immobilized at each spot, such as those described in provisional U.S. application Ser. No. 60/111,961 (Attorney Docket No. 9598-068-888) incorporated herein by reference, may be advantageously used in the context of the present invention.

Oligonucleotides may be organized into arrays, and these arrays may include all or a subset of all probes of a given length, or sets of probes of selected lengths. Hydrophobic partitions may be used to separate probes or subarrays of probes. Arrays may be designed for various applications (e.g. mapping, partial sequencing, sequencing of targeted regions for diagnostic purposes, mRNA sequencing and large scale sequencing). A specific chip may be designed for a particular application by selecting a combination and arrangement of probes on a substrate.

In one embodiment, the substrate which supports the array of probes is partitioned into sections so that each probe in the array is separated from adjacent probes by a physical barrier which may be, for example, a hydrophobic material. In a preferred embodiment, the physical barrier has a width of from 100 μm to 30 μm. In a more preferred embodiment, the distance from the center of each probe to the center of any adjacent probes is 325 μm. These arrays of probes may be "mass-produced" using a nonmoving, fixed substrate or a substrate fixed to a rotating drum or plate with an ink-jet deposition apparatus, for example, a microdrop dosing head; and a suitable robotic system, for example, an anorad gantry. Alternatively, the probes may be fixed to a three-dimensional array (see, e.g., Example 33 of WO 99/09217 published Feb. 28, 1999, incorporated herein by reference).

The probes in these arrays may include spacers that increase the distance between the surface of the substrate and the informational portion of the probes. The spacers may be comprised of atoms capable of forming at least two covalent bonds such as carbon, silicon, oxygen, sulfur, phosphorous, and the like, or may be comprised of molecules capable of forming at least two covalent bonds such as sugar-phosphate groups, amino acids, peptides, nucleosides, nucleotides, sugars, carbohydrates, aromatic rings, hydrocarbon rings, linear and branched hydrocarbons, and the like.

Reusable arrays may be produced as described in Int'l Publication No. WO 98/31836 published Jul. 23, 1998 and WO 99/09217 published Feb. 28, 1999, both of which are incorporated herein by reference. See, e.g., Example 18 of WO 98/31836. A reusable Format 3 SBH array may be produced by introducing a cleavable bond between the fixed and labeled probes and then cleaving this bond after a round of Format 3 analyzes is finished. If the labeled probes contain ribonucleotides or if a ribonucleotide is used as the joining base in the labeled probe, this probe may subsequently be removed, e.g., by RNAse or uracil-DNA glycosylate treatment, or NaOH treatment. In addition, bonds produced by chemical ligation may be selectively cleaved.

Other variations include the use of modified oligonucleotides to increase specificity or efficiency, cycling hybridizations to increase the hybridization signal, for example by performing a hybridization cycle under conditions (e.g. temperature) optimally selected for a first set of labeled probes followed by hybridization under conditions optimally selected for a second set of labeled probes. Shifts in reading frame may be determined by using mixtures (preferably mixtures of equimolar amounts) of probes ending in each of the four nucleotide bases A, T, C and G.

Rather than being ordered on an array, the probes may alternatively be complexed (covalent or noncovalent) to discrete particles wherein the particles can be grouped into a plurality of sets based on a physical property. In a preferred embodiment, a different probe is attached to the discrete particles of each set, and the identity of the probe is determined by identifying the physical property of the discrete particles. In an alternative embodiment, the probe is identified on the basis of a physical property of the probe. The physical property includes any that can be used to differentiate the discrete particles, and includes, for example, size, fluorescence, radioactivity, electromagnetic charge, or absorbance, or label(s) may be attached to the particle such as a dye, a radionuclide, or an EML. In a preferred embodiment, discrete particles are separated by a flow cytometer which detects the size, charge, flourescence, or absorbance of the particle. See, e.g., Example 36 of WO 99/09217 published Feb. 28, 1999, incorporated herein by reference.

The probes complexed with the discrete particles can be used to analyze target nucleic acids. These probes may be used in any of the methods described herein, with the modification of identifying the probe by the physical property of the discrete particle. These probes may also be used in a Format 3 approach where the "free" probe is identified by a label, and the probe complexed to the discrete particle is identified by the physical property. In a preferred embodiment, the probes are used to sequence a target nucleic acid using SBH.

Probes may be labeled with different labels and multiplexed in a set so that each probe of a set can be differentiated from the other probes in the same set by its label. See, e.g., Example 30 of WO 98/31836, incorporated herein by reference. For example, different radioisotopes, fluorescent labels, chromophores, or EMLs, or mixtures thereof may be used for multiplexing.

c. Selection of Sets of Probes To Be Hybridized to Target Nucleic Acid

Sets of probes to be hybridized to target nucleic acid may be selected as described in Int'l Publication No. WO 98/31836 published Jul. 23, 1998 and WO 99/09217 published Feb. 28, 1999, both of which are incorporated herein by reference. See, e.g., Examples 1 through 4, 11 through 17, and 19 through 29 of WO 98/31836.

A universal set of probes includes sufficient probes to analyze a DNA fragment with prespecified precision, e.g. with respect to the redundancy of reading each base pair ("bp"). A small subset of probes may be selected that is still sufficient for reading every bp in any sequence with at least one probe. For example, 12 of the 16 possible 2-mers are sufficient to read 2 consecutive bases. A small subset for 7-mers, 8-mer and 9-mers for sequencing double stranded DNA may be about 3000, 10,000 and 30,000 probes, respectively.

A less than universal set of probes may also be selected to identify a target nucleic acid of known sequence and/or to identify alleles or mutants of a target nucleic acid with a known sequence. Such a set of probes contains sufficient probes so that every nucleotide position of the target nucleic acid is read at least once. Alleles or mutants are identified by the loss of binding of one of the "positive" probes. The specific sequence of these alleles or mutants may then be determined by interrogating the target nucleic acid with sets of probes that contain every possible nucleotide change and combination of changes at these probe positions.

Sets of probes may comprise 2 probes or more, 50 probes or more, preferably 100 probes or more, and more preferably 256 probes or more.

DNA or allele identification and a diagnostic sequencing process may include the steps of: selecting a subset of probes from a dedicated, representative or universal set to be hybridized with target nucleic acid(s) optionally disposed in an array; performing hybridization and scoring of the hybridization results, which can be carried out in parallel with multiple subsets of probes selected in step 1; optionally processing the hybridization results to obtain a final sequence analysis or to determine whether additional probes should be hybridized; and repeating the hybridization, scoring and optionally the processing steps for the remaining probes in the set until a final sequence analysis is obtained.

A known target nucleic acid may be sequenced as follows. One embodiment involves hybridization to the target of a sufficient set of probes that covers every base in the known reference sequence at least once. For this purpose, a specific set of probes may be synthesized for a standard sample. The results of hybridization with such a set of probes reveal whether and where mutations (differences) occur in non-standard samples. Further, this set of probes may include "negative" probes to confirm the hybridization results of the "positive" probes. To determine the identity of the changes, additional specific probes may be hybridized to the sample. This additional set of probes will have both "positive" (the mutant sequence) and "negative" probes, and the sequence changes will be identified by the positive probes and confirmed by the negative probes.

In another embodiment, all probes from a universal set may be hybridized to the target. Use of a universal set of probes in a multistep process allows scoring of a relatively small number of probes per sample; as noted above, successive hybridizations involving a first step of computing an optimal subset of probes to be hybridized first and, then, on the basis of the obtained results, a second step of determining which of the remaining probes in the set should be hybridized next. Both sets of probes may have negative probes that confirm the positive probes in the set. Further, the sequence that is determined may then be confirmed in a separate step by hybridizing the sample with a set of negative probes identified from the SBH results.

For SBH of a random nucleic acid sequence using errorless data (i.e., no experimental false negatives and no experimental false positives), the read length of the target nucleic acid is defined by the probe length if no additional information to the list of positive probes, K bases in length, is used (see Table 1). The limits are defined by the probability of repeating in a target nucleic acid a K-1 oligonucleotide sequence used for sequence assembly in a target sequence. Sequences with a biased content of nucleotides (e.g. AT or GC rich sequences) need even longer probes. The number of probes per base pair for optimal read length exponentially increases as longer probes are used, and an extremely small percentage of probes is positive. The explanation for this almost paradoxical inefficiency of long probes is in the completeness criteria. The incomplete assembly of sequences longer than 100 bases with 7-mers requires combining accurately determined sequences of about 20 bases in length in a different order. The incomplete assembly of sequences longer than 25 kb with 15-mers means that only the order of accurately determined sequences of 2-5 kb (3×6× gel read length) may be incorrect. The missing information to map sufficiently long sequence segments may be easily provided (for example by restriction analysis) extending the potential target read length of 10-mers from 800 bases to over 2 kb, and 15-mers from 25 kb to over 200 kb.

TABLE 1

Relationship of probe length, target sequence read length and % positive probes

| No. bases in probe | No. possible probes | No. bases in target that can be read (for >90% assembly rate) | No. probes/ base | % probes that are positive |
|---|---|---|---|---|
| 7 | 16,384 | 100 | 160 | 0.600 |
| 8 | 65,536 | 200 | 320 | 0.300 |
| 9 | 262,144 | 400 | 640 | 0.150 |
| 10 | 1,048,576 | 800 | 1,280 | 0.075 |
| 11 | 4,194,304 | 1,600 | 2,560 | 0.037 |
| 12 | 16,777,216 | 3,200 | 6,120 | 0.019 |
| 13 | 67,108,864 | 6,400 | 12,240 | 0.009 |
| 14 | 268,435,456 | 12,800 | 24,480 | 0.005 |
| 15 | 1,073,741,824 | 25,600 | 48,960 | 0.002 |

The use of an array of samples avoids consecutive scoring of many oligonucleotides on a single sample or on a small set of samples. This approach allows the scoring of more probes in parallel by manipulation of only one physical object. Subarrays of DNA samples 1000 bp in length may be sequenced in a relatively short period of time. If the samples are spotted at 50 subarrays in an array and the array is reprobed 10 times, 500 probes may be scored. In screening for the occurrence of a mutation, enough probes may be used to cover each base three times. If a mutation is present, several covering probes will be affected. The use of information about the identity of negative probes may map the mutation with a two base precision. To solve a single base mutation mapped in this way, an additional 15 probes may be employed. These probes cover any base combination for two questionable positions (assuming that deletions and insertions are not involved). These probes may be scored in one cycle on 50 subarrays which contain a given sample. In the implementation of a multiple label scheme (i.e., multiplexing), two to six probes, each having a different label such as a different fluorescent dye, may be used as a pool, thereby reducing the number of hybridization cycles and shortening the sequencing process.

In more complicated cases, there may be two close mutations or insertions. They may be handled with more probes. For example, a three base insertion may be solved with 64 probes. The most complicated cases may be approached by several steps of hybridization, and the selecting of a new set of probes on the basis of results of previous hybridizations.

If subarrays to be analyzed include tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel facilitates scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be analyzed. These targets may represent pools of fragments such as pools of exon clones.

d. Designing and Optimizing Pools of Probes

Several considerations are involved in generating the pools of probes. First, the basic logic of pooling is to avoid putting together related pairs or sets of probes; that is, the pools should be designed to minimize offset overlaps within the sets. In particular, for probes of length K, the probes in a pool should preferably not contain overlaps of K-1 nucleotides. For example if the AAAA(C,T)AAA pair of probes is present in one pool, the overlapping AAA(C,T)AAAC pair of probes should not be in the same pool. Additionally, probes in a pool are preferably not reverse complements of any other probes in the same pool. However, probes that are degenerate at specific internal positions may be placed in the same set. This property provides for particularly efficient methods of producing the probes, as many probes may be produced at once as degenerate pools of probes. For example, a pool of eight 7-mer probes might comprise probes of the sequence BYBRBSB, where B is a nucleotide that is the same for all probes in the pool, Y is C or T, R is A or G, and S is-C or G. Similarly, a pool of sixteen 10-mers might comprise four degenerate positions with two mixed nucleotides at each position. Changing the combinations of the two mixed nucleotides, and the locations of the degenerate positions, is used to generate all pools. The preferred strategy is to have not more than two mixed nucleotides per degenerate position, although in some cases a degenerate position may contain three or four mixed nucleotides. Additionally, the probes in a pool should preferably vary at more than one position, and more preferably at more than two positions.

In an alternative embodiment, the probes maybe synthesized individually and then mixed into appropriate pools; this method is particularly suited for small sets of shorter probes. In many cases, it will also be possible to construct the pool using simple random assignment of the probes to pools; if the number of pools is sufficiently large, then random assignment should generally yield pools that meet the above criteria.

Pools may also be efficiently prepared by mixed base synthesis. Maximal randomization is achieved if not more two different bases are incorporated at one position, and all 6 possible base mixes (A+T, A+C, A+G, T+C, T+G, C+G) are used equally. In this synthesis of pools, a small number of probes per pool will differ by one base only (one per each degenerated base position). The preparation of pools in mixed synthesis is applicable both for arrays of attached probes and for pools of labeled probes. The number of independent probe synthesis may be reduced from millions (see Table 3) to thousands if each pool is prepared in one reaction.

An example of mixed synthesis of 3-mer probes grouped in 8 pools, each containing eight 3-mers, is illustrated below. These pools should represent all 64 3-mer probes without repeating any probe in two pools. The pools may be prepared in 8 synthesis reactions by incorporating specified mixes of two nucleotides. There are 6 possible two-base mixtures (a+t, a+c, a+g, c+g, c+t, and g+t). Pool designing starts with the first base position. All four bases at the first position may be represented by synthesizing two pools of two-bases, e.g. (a+t) and (c+g). Each of these two bases in two pools may be extended to form four pools of 2-mers; in the next round of extension four pools of 2-mers may be extended to form eight 3-mer pools.

| | | 3-mer probes in each pool | overlapping probes |
|---|---|---|---|
| Pool set 1 | | | |
| 1. | (a + t) (a + g) (a + c) | (aaa, aac, aga, agc, taa, tac, tga, tgc) | aaa/aac, taa/aaa, |
| 2. | (a + t) (a + g) (g + t) | (aag, aat, agg, agt, tag, tat, tgg, tgt) | aag/agg, aag/agt |
| 3. | (a + t) (c + t) (a + g) | | |
| 4. | (a + t) (c + t) (c + t) | | |
| 5. | (c + g) (a + c) (a + g) | | |
| 6. | (c + g) (a + c) (c + t) | | |
| 7. | (c + g) (g + t) (a + c) | | |
| 8. | (c + g) (g + t) (g + t) | | |
| Pool set 2 | | | |
| 1. | (a + t) (a + g) (a + t) | (aaa, aat, aga, agt, taa, tat, tgs, tgt) | (aaa/aat, taa/aaa |
| 2. | (a + t) (a + g) (c + g) | (aac, aag, agc, agg, tac, tag, tgc, tgg) | (aag/agc, aag/agg |
| 3. | (a + t) (c + t) (a + c) | | |
| 4. | (a + t) (c + t) (g + t) | | |
| 5. | (c + g) (a + c) (a + g) | | |
| 6. | (c + g) (a + c) (c + t) | | |
| 7. | (c + g) (g + t) (a + t) | | |
| 8. | (c + g) (g + t) (c + g) | | |

As illustrated above, none of pools in pool set 1 have two positions with the same mix of two bases, In the case of pool set 2, the first and last pool have the same mix at the first and the last position. Pools like (a+t) (a+t).(a+t) (aaa, aat, ata, att, taa, tat, tta, ttt) should be avoided because they will contain too many mutual overlaps (aaa/aat, aat/ata, ata/taa, taa/aaa, tat/ata, etc.)

Another example of mixed synthesis of 10-mer probes grouped in pools of 64 10-mers comprising all individual bases and all combinations of two bases is as follows: (a,c)t(c,g)(g,t)a(a,g)cg(a,t)(c,t)

A combination of low complexity pools can also be prepared by mixed synthesis and pooling of pools.

The main possible negative result from using a set of pools of probes, when compared to the use of a set of individual probes, is that a particular set of positive pools can define not only the real sequence (the reason that those pools are positive) but also a different, false sequence that happened to share the same set of positive pools. Thus, the pooling would be non-informative if it contained sets of overlapping probes representing two different sequences in the same pools. The random pooling of probes minimizes that happening. Of course, in any set of randomly generated pools, many similar pools may be generated, and exceptional cases may arise. Thus, randomly generated pools may preferably be further optimized by extensive testing of sequences of certain length (for example, 10-30 nucleotides). The optimal results would be achieved if all possible sequences in such a size range are tested. For each of these sequences, positive pools are defined and then all possible sequences that can be generated from the same positive set of pools are assembled. If sequences of that length other than the starting sequence are formed, then some of the probes defining these sequences are moved to other pools. The process may be run in large number of optimization cycles to create optimum sets of pools of probes.

A flowchart of a pool selection process 100 employing the above criteria is illustrated in FIG. 1. The process 100 can be implemented by a human operator and/or a computing device (described below). The process 100 begins by generating a set of pools (step 102). In this example, sixteen pools, each containing sixty-four probes of length five, are generated. Of course, a person of ordinary skill in the art will readily appreciate that any number of pools containing any number of probes of any length may be similarly generated.

Next, at step 104, the process 100 retrieves the first pool in the set of generated pools. The retrieved pool is then examined in three different ways. First, the pool is examined to determine if any four positions of one probe contain the same bases as any other probe in the same pool (step 106). Second, the pool is examined to determine if any four consecutive positions of one probe match any four consecutive positions of another probe in the same pool (step 108). Third, the pool is examined to determine if there are any reverse complements (step 110).

If the first pool passes all of these tests (i.e., the NO path on steps 106, 108, and 110), and there are more pools in this set to be tested (step 112), then the process 100 moves on to the next pool in this set at step 104. If all of the pools in a particular set pass the above three tests, the set is recorded as a preferred set of pools at step 114. If any of the tests fail (i.e., a YES path on step 106, 108, or 110), and there are more sets of pools to be generated (step 116), then the process generates the next set of pools at step 102 and repeats the process. Step 116 may force the process to be exhaustive, it may try only certain predetermined sets, or it may try a predetermined number of sets.

If no valid set of pools is determined after all sets have been tested, the process indicates this result at step 118. In the event that no valid set of pools is determined, the process may modify the criteria used by steps 106, 108, and/or 110 to increase the likelihood that a valid set of pools will be found. For example, step 106 maybe modified to determine if any three positions of one probe contain the same bases as another probe. Step 106 could also be modified to take the YES path only if three or more probes contain the same bases in a predetermined number of positions. Similarly, the requirement of steps 108 and/or 110 may be loosened by reducing the number of positions and/or increasing the number of matches needed to produce a YES result.

The desired number of pools and number of probes in each pool may be determined as follows. The pools are designed with a specified level of redundancy R, representing the number of score measurements (hybridizations) required to identify each nucleotide of a sequence. Positive probes are very rare (1 in 100 to 1 in 50,000, see Table 1). Thus, even after substantial probe pooling only a fraction of pools will be positive. If random pools of probes are used in SBH for de novo sequencing, and completely errorless data is assumed, the optimal pool number and pool size can be determined by the probability that several consecutive false positive overlapping probes will occur. The fraction of pools expected to give a positive result (Fp) is P/T, where P is the total number of probes initially scored as positive and T is the total number of probes in the set. The Fp is inversely related to the level of redundancy R (Fp=1/R). The probability that a probe having a length of K bases (which is also referred to as a K-mer or a K-tuple) was falsely scored is thus 1/R, and therefore the probability that two falsely scored probes will consecutively overlap by chance (the "POC") is 4/R (or 4×Fp). R must thus be greater than 4; otherwise, the probability of false overlaps will be equal to 1 (4×¼). Preferably, R is less than about 100, or less than about 50, or less than about 20, or less than about 10, or about 5 or less, or between 4 and about 5. When the R value is about 10, then 1/R=0.1, and thus about 10% of all pools are scored as positive when hybridized with a target sequence. For other sequencing applications, e.g., when the reference sequence is known, R may be very low (e.g., close to 4).

An R value of 5 still provides acceptable sequencing results, even for de novo sequencing. Because many consecutive false overlaps are required in order to assemble an incorrect sequence, the tolerable probability of false overlaps may be very close to 1 (i.e., Fp may be close to ¼). For example, if Fp=⅕ then the POC, i.e. the probability of a false overlap occurring by chance, is ⅘ (4×Fp) and assembly of an incorrect target sequence of length L is $POC^L$. For a 100 base target sequence, probability of assembling an incorrect sequence is about $2\times10^{-10}$ for each attempt to assemble sequence (where for 10-mers, about $2\times10^5$ attempts are made to assemble sequence, or for 15-mers, about $2\times10^8$ attempts).

Once the value of R is chosen, it can be used to determine the appropriate number of pools and number of probes per pool. For a target sequence of a given length L, the total number of pools required is R×L. One of skill in the art would then determine the appropriate probe length K required to sequence a target of length L. Since the total number of probes in the complete set of K-mers is $4^k$, the number of probes in each pool is then given by $4^k/(R\times L)$. The number of probes in all positive pools combined is $4^k/R$, since only one in R pools is positive. For example, if the desired redundancy is R=10 and the target is of length L=3000 nucleotides, then K=12 and the total number of pools desired is approximately 10×3000=30,000, and the number of probes in each pool is $4^{12}/30,000=560$ probes.

The pools of probes may be generated each time sequencing of a target is desired. In practice, however, the present invention will probably be most useful if "standard" sets of pools are used. For a given sequence of length L, one of skill in the art will know what probe length K is required. All sequences that can be sequenced by probes of length K may then use the same set of pools of probes of length K. The number of pools and number of probes in each pool of the standard set will be determined by the maximal sequence length that may be determined by probes of length K. For example, sequencing DNA targets having lengths between 1601 and 3200 nucleotides requires probes of length K=12, and the total set of probes of length 12 is $4^{12}=16,777,216$ probes. Since the maximal sequence length L that may be sequenced by 12-mers is 3200 nucleotides, the maximal total number of pools required is 10×3200=32,000. The number of probes in each pool is then 16,777,216/32,000=525. Thus, the "standard" set of pools for sequencing DNA targets having lengths between 1601 and 3200 nucleotides will comprise 32,000 pools of probes, each containing 525 probes. The specific probes that comprise each pool are then selected according to the rules set out above. Preferably, the pools are also optimized according to the method described above. Once the pools are so defined and constituted, they can then be used for any sequence in the particular length range. Similar "standard" sets can be defined and optimized for any desired sequence length.

An incorrect sequence may be assembled from a small number of false positive probes if these false positive probes overlap with some true positive probes. Two classes of these false positive probes are illustrated in Table 2 below 1) Assembly of an incorrect sequence containing a single base substitution or insertion compared to the correct sequence requires a specific set of K false positive overlapped probes. Assembly of an incorrect sequence containing multiple base substitutions or insertions requires more than K probes. Assembly of an incorrect sequence containing a deletion of any size requires K-1 probes. Fewer than K false probes may be sufficient if the mutation is in a tandem repeat. There are about 7L possible different one-base changes.

2) Branching points may be created at K-2 or shorter repeats; for the K-2 case, a minimum of 4 specific false positive probes is required, but it can occur only in a few places in the target sequence; for the K-3 case, 8 probes are required and only dozen cases can exist in a target sequence of the appropriate length for K-mer probes;

TABLE 2

Specific false positive 5-mer probes causing branching.

```
                                       (SEQ ID NO:3)
      1)  atctgtgtctgaagtagtcc
             tgtgg
              gtggc
               tggct
                ggctg
                 gctga

                                       (SEQ ID NO:4)
          atctgtggctgaagtagtcc

                                       (SEQ ID NO:5)
2) a) bbbbbbatttcbbbbbgcactbbbbgtttgbbbacacgbbbbb
            atttg     gcacg    gtttc   acact

                                       (SEQ ID NO:6)
   b) bbbbbbatttgbbbacactbbbbgtttcbbbbbgcacgbbbbb
            atttc   acacg    gtttg     gcact
```

1) Only five (K = 5) false positive probes, listed above, are sufficient to make a single base T to G substitution.
2) Only four specific false positive probes can create a branching point for two pairs of K-2 repeats (a ttt pair and a cac pair). If these pairs of repeats are four bases long (equal to K-1 for 5-mers), they will represent regular branch points. In this case (K-2 repeats), without these four false positive probes a unique sequence would be assembled. If the listed single base mismatch probes are scored, a second sequence is also assembled where segments tttcbbbbbgccc and tttgbbbaccc from the real sequence are switched. To assemble this incorrect sequence false probes are incorporated and four correct probes are seen as false positive. The same conditions apply for all sequences having any base at positions denoted by b.

In these specific illustrated cases, the probability of one base extension is equal to Fp, not to 4Fp, because a specific probe that overlaps by K-1 is required. Thus, for Fp=⅕, the probability of assembling an incorrect sequence containing a deletion (the most prevalent error) is $(1/5)^{K-1}$. For sequencing a target of 800 bases with 10-mers, there are about 800×800/10 ($6.4\times10^4$) possible deletions shorter than 80 bases, and the probability of each is $(1/5)^9$ or $5\times10^{-7}$. Thus, a deletion will assemble only once in more than 30 experiments; for sequencing a target of 3200 bases with 12-mers, one in 50 experiments will have a sequence containing a deletion.

It appears an Fp of 1/5 (i.e., a redundancy of about 5 or less) or more provides satisfactory results. Table 3 shows the number and the size of pools for probes ranging from 10 to 17 bases in length assuming a minimal redundancy of 5 scores per base. Obviously, for the longer probes, the large pools require readers with high sensitivity, very specific full match hybridization, and proper computation software and hardware for fast sequence assembly. Statistical analysis shows that over 100 kb may be sequenced in one reaction with 500,000 pools of 32,000 17-mers each, providing that the necessary sensitivity and specificity in scoring positive pools are achieved.

TABLE 3

| Number and size of pools for Fp = 1/5 | | | | |
|---|---|---|---|---|
| Probe length | Number of probes | Read length | Number of pools | Probe/pool |
| 10 | 1 M | 800 | 4,000 | 250 |
| 11 | 4 M | 1,600 | 8,000 | 500 |
| 12 | 16 M | 3,200 | 16,000 | 1,000 |
| 13 | 64 M | 6,400 | 32,000 | 2,000 |
| 14 | 256 M | 12,800 | 64,000 | 4,000 |
| 15 | 1 B | 25,600 | 128,000 | 8,000 |
| 16 | 4 B | 51,200 | 256,000 | 16,000 |
| 17 | 16 B | 102,400 | 500,000 | 32,000 |

The redundancy of 5 scores per target nucleic acid base is very close to 4 measurements per base required for gel and other methods that experimentally provide one measurement for each of four nucleotides at each position in the target nucleic acid. The redundancy of measurements should not be mistaken for the number of positive probes per target base pair. In SBH experiment, the number of positive probes (i.e., the number of reads) per target base is equal to the number of bases in the probes used (K). In contrast, gel sequencing reads each base only once. Thus for probes 10-20 bases in length and Fp=1/5, SBH provides 8-16 fold more passes than gel sequencing, which should increase the accuracy of identifying (or "calling") bases.

e. Preparation of Target Nucleic Acid

Target nucleic acid may be prepared, optionally labeled, and optionally disposed on a solid substrate as described in Int'l Publication No. WO 98/31836 published Jul. 23, 1998 and WO 99/09217 published Feb. 28, 1999, both of which are incorporated herein by reference. See, e.g., Examples 7 through 8 and 15 of WO 98/31836. Nucleic acids and methods for isolating and cloning nucleic acids are well known to those of skill in the art. See e.g., Ausubel et al., *Current Protocols in Molecular Biology, Vol.* 1-2, John Wiley & Sons (1989); and Sambrook et al., Molecular Cloning A Laboratory Manual, 2nd Ed., Vols. 1-3, Cold Springs Harbor Press (1989), both of which are incorporated by reference herein.

A nucleic acid sample to be sequenced may be fragmented or otherwise treated (for example, by the use of recA) to avoid hindrance to hybridization from secondary structure in the sample. The sample may be fragmented by, for example, digestion with a restriction enzyme such as Cvi JI, physical shearing (e.g. by ultrasound or low pressure), treatment with uracil DNA glycosylase, or by NaOH treatment. The resulting fragments may be separated by gel electrophoresis and fragments of an appropriate length, such as between about 10 bp and about 40 bp, may be extracted from the gel. The minimal length of a nucleic acid fragment suitable for SBH analysis is about 2×K, where K is the probe length. Nucleic acid may also be obtained by a process that yields a single stranded product, e.g., asymmetric PCR (as described in co-owned U.S. Application Ser. No. 60/148,942 filed Aug. 13, 1999 entitled "The Use of Asymmetric PCR for SBH."

Even short nucleic acid fragments can provide useful information. For example, mutations in a gene such as single nucleotide POLYMORPHISMS or other allelic variants can be identified from a small fragment of the gene. For example, if the location of the mutation is known, PCR can be used to amplify a suitable fragment that includes the location of interest. Even if large amounts of DNA are to be analyzed (e.g., for genotyping of a genome or portion thereof), the preparation of low complexity targets is possible by, e.g., cleaving the genomic DNA with one or two restriction enzymes to generate 3 million fragments of about 1000 bp, ligating these fragments to adaptors bound to a solid support, then cleaving the 1000 bp fragments again down to about 30 bp fragments. This results in greatly reduced target complexity and provides short fragments that potentially encode 1 million polymorphic sites.

As another example, SBH analysis can be used to detect the presence or expression of a gene or mRNA in a sample even if only the 3' or 5' end of the gene or mRNA is analyzed. Particularly for mRNA, oligo-dT priming can be used to generate small fragments of the 3' end of mRNAs which can then be analyzed by SBH.

In a preferred embodiment, the "fragments" of the nucleic acid sample cannot be ligated to other fragments in the pool. Such a pool of fragments may be obtained by treating the fragmented nucleic acids with a phosphatase (e.g., calf intestinal phosphatase). Alternatively, nonligatable fragments of the sample nucleic acid may be obtained by using random primers (e.g., $N_5$-$N_9$, where N =A, G, T, or C) in a Sanger-dideoxy sequencing reaction with the sample nucleic acid. This will produce fragments of DNA that have a complementary sequence to the target nucleic acid and that are terminated in a dideoxy residue that cannot be ligated to other fragments.

Partitioned membranes allow a very flexible organization of experiments to accommodate relatively larger numbers of samples representing a given sequence type, or many different types of samples represented with relatively small numbers of samples. A range of 4-256 samples can be handled with particular efficiency. Subarrays within this range of numbers of dots may be designed to match the configuration and size of standard multiwell plates used for storing and labeling oligonucleotides. The size of the subarrays may be adjusted for different number of samples, or a few standard subarray sizes may be used. If all samples of a type do not fit in one subarray, additional subarrays or membranes may be used and processed with the same probes. In addition, by adjusting the number of replicas for each subarray, the time for completion of identification or sequencing process may be varied.

f. Hybridization of Pools of Probes

In use, the defined pools of probes are then hybridized with the target nucleic acid. The hybridization conditions used will depend upon, among other factors, the G+C content of the sequence of interest and the lengths of the probes in the pools. Hybridization and washing conditions may be selected to allow detection of substantially perfect match hybrids (such as those wherein the fragment and probe hybridize at six out of seven positions), may be selected to allow differentiation of hybridization signals from perfectly complementary (full match) probes and single base pair mismatch probes, or may be selected to permit detection only of perfectly matched hybrids. Hybridization and washing conditions useful for discriminating between perfect complements and mismatches in the informational content of the probes for a variety of hybridization arrays have been described in the art. For example, hybridization and washing conditions useful for discriminating complementary and mismatched hybrids in a variety of SBH and other applications are described in U.S. Pat. No. 5,525,464 to Drmanac et al., and Int'l Publication Nos. WO 95/09248, WO 98/31836 published Jul. 23, 1998, and WO 99/09217 published Feb. 28, 1999, all of which are incorporated herein by reference. A particularly detailed discussion of the theoretical and practical considerations involved in determining hybridization conditions, and including a discussion of the advantages of low-temperature washing steps, may be found in WO 98/31836, incorporated herein by reference, particularly pages 50-62 and Examples 9 through 10, 12, 13, 15 and 26. See also, e.g., Example 37 of WO 99/09217. Additional guidance may be found in Harmes and Higgins, Nucleic Acid Hybridization: A Practical Approach, 1985, IRL Press, Oxford, England.

Suitable hybridization conditions may be routinely determined by optimization procedures or pilot studies. Such procedures and studies are routinely conducted by those skilled in the art to establish protocols for use in a laboratory. See e.g., Ausubel et al., *Current Protocols in Molecular Biology*, Vol. 1-2, John Wiley & Sons (1989); Sambrook et al., Molecular Cloning A Laboratory Manual, 2nd Ed., Vols. 1-3, Cold Springs Harbor Press (1989); and Maniatis et al., *Molecular Cloning: A Laboratory Manual*, Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

In embodiments wherein the labeled and immobilized probes are not physically or chemically linked, detection may rely solely on washing steps of controlled stringency. Under such conditions, adjacent probes have increased binding affinity because of stacking interactions between the adjacent probes. Conditions may be varied to optimize the process as described above.

In embodiments wherein the immobilized and labeled probes are ligated, ligation may be implemented by a chemical ligating agent (e.g. water-soluble carbodiimide or cyanogen bromide), or a ligase enzyme, such as the commercially available $T_4$ DNA ligase may be employed. The washing conditions may be selected to distinguish between adjacent versus nonadjacent labeled and immobilized probes exploiting the difference in stability for adjacent probes versus nonadjacent probes.

Agents which destabilize the binding of complementary polynucleotide strands (decrease the binding energy), or increase stability of binding between complementary polynucleotide strands (increase the binding energy) may also be used. In preferred embodiments, the agent is a trialkyl amrnonium salt, sodium chloride, phosphate salts, borate salts, organic solvents such as formamide, glycol, dimethylsulfoxide, and dimethylformamide, urea, guanidinium, amino acid analogs such as betaine, polyamines such as spermidine and spermine, or other positively charged molecules which neutralize the negative charge of the phosphate backbone, detergents such as sodium dodecyl sulfate, and sodium lauryl sarcosinate, minor/major groove binding agents, positively charged polypeptides, and intercalating agents such as acridine, ethidium bromide, and anthracine. In a preferred embodiment, an agent is used to reduce or increase the $T_m$ of a pair of complementary polynucleotides. In a more preferred embodiment, a mixture of the agents is used to reduce or increase the $T_m$ of a pair of complementary polynucleotides. In a most preferred embodiment, an agent or a mixture of agents is used to increase the discrimination of perfect matches from mismatches for complementary polynucleotides. In a preferred embodiment, the agent or agents are added so that the binding energy from an AT base pair is approximately equivalent to the binding energy of a GC base pair. The energy of binding of these complementary polynucleotides may be increased by adding an agent that neutralizes or shields the negative charges of the phosphate groups in the polynucleotide backbone. See, e.g., Example 37 of WO 99/09217 published Feb. 28, 1999, incorporated herein by reference.

g. Sequence Assembly

Data may be scored and analyzed and sequence assembled generally as described in Int'l Publication No. WO 98/31836 published Jul. 23, 1998 and WO 99/09217 published Feb. 28, 1999, both of which are incorporated herein by reference. See, e.g., Examples 11 through 17 and 28 through 29 of WO 98/31836. For example, subfragments may be generated by overlapping positive probe sequences until an ambiguity arises because of a branch point (i.e., a probe sequence is repeated in the target nucleic acid), or because of a repetitive sequence longer than the probe, or because of an uncloned segment. Subfragments may be linearly ordered to regenerate the complete sequence of the target nucleic acid fragment by a variety of techniques known in the art, e.g., hybridization with longer probes spanning the site of overlap alternatives, competitive hybridization, ligation of alternative end to end pairs of probes spanning the site of ambiguity or single pass gel analysis.

The assembly process using information from pools of probes is similar to that of conventional SBH in the presence of many false positive probes. Ideally (where there are no false negatives and no branch points), the result of this sequence assembly would be one long correct sequence and shorter incorrect sequences or individual probes that cannot be extended by overlapping with other probes. The creation of many more false positive probes than true positive probes by pooling of probes causes many more shorter sequences to be assembled. Sequences are particularly prone to error at their 5' and 3' ends, so that knowledge of correct 5' or 3' end sequences (for example primer sequences) allows better selection of the correct sequence. In addition, knowledge of the real length of the target sequence allows better selection of a correct sequence.

Data from the positive pools of probes may be analyzed by an algorithm, preferably performed on a computer. In one embodiment, the analysis begins from a probe of known sequence, for example a PCR primer that was used to generate the target nucleic acid. Alternatively, when no sequence is known, all probes in a selected positive pool are used as starting probes. The computer then identifies positive pools that contain probes having sequence that contiguously overlap the sequence of the starting probe(s). Preferably, the overlaps are identified in a K-1 fashion (i.e., probes that, when the contiguous region of overlap is aligned, have single nucleotide overhangs); however, in some embodiments (particularly involving accounting for false negative data, i.e., missing probes), K-2 or larger overlaps may be used, preferably K-2 overlaps. The standard K-mer analysis is described in U.S. Pat. Nos. 5,202,231 and 5,525,464. If the pools are designed properly, each pool should contain at most one probe that potentially overlaps the starting probe. Ideally, only one pool is positive, and the next nucleotide is thus identified unambiguously. In this case, the process is repeated with the next overlapping sequence, and so on through the entire sequence.

Because some false negatives probes (i.e., missing probes) are expected, the sequence assembly algorithm must allow some K-2 or shorter overlaps. If only K-1 overlaps are used in every assembly step, then Fp must be reduced four fold by using four fold smaller pools. If sequence is assembled only using K-2 overlaps, the assumed false negative rate is 50%. Typical experimental false negative rates are more likely to be between 3 and 10%, so that many fragments of e.g., 20-50 bases may be assembled without using a K-2 overlap, and longer sequences may be assembled by allowing a limited use (e.g., one per 20 sequence extension cycles, on average) of K-2 overlaps. Although sequence assembly when there are two consecutive false negative probes requires a K-3 overlap, that situation will happen very rarely (e.g., it may occur when a region of test DNA is inaccessible for hybridization). Thus, a percentage of false negative probes that is less than 10% false negative probes does not necessarily require a substantial increase in score redundancy per base (which in turn would require use of more and smaller sized pools).

Since the probes in a given pool are indistinguishable, a pool may give a positive result because a different probe in the pool hybridized to a different part of the target sequence. These "false" positives occur at frequency of 1/R. In such a case, two possibilities (or, in rare cases, even three or four) exist for the next nucleotide. The process is then repeated for each of these possible forks (also called branches). In-most cases, no positive pools will overlap the sequence from the incorrect pool, and thus that fork will be discarded. However, at a probability of $1/R^2$, two consecutive incorrect positive pools may be found. In this case, the process is repeated for all positive forks. The probability of a fork extending b incorrect nucleotides is $1/R^b$, and thus false forks quickly disappear from the analysis, and the sequence may then be unambiguously determined. For R=10, by the fourth incorrect position only a 1/10,000 chance of continuing remains. The normal problems of branch ambiguity found in SBH still occur, and these may be resolved by art-recogniized methods (see, for example, Int'l Publication No. WO 98/31836, incorporated herein by reference). In particular, the pooling method facilitates the use of longer probes, which drastically reduces the number of branch points that need be resolved.

The probability of a fork in at least C cycles of overlaps ($_Cc$) is $(_4/R)^C$, and the average number of false forks of C or more cycles is $[(4^k)/R]\times P_C$. For R=8, K=12, and C=20, $P_C(20)=10^{-6}$, and the number of false C(20) or longer forks is $(16\times 10^6)/8\times(10^{-6})=2$. In this example, sequences of about 3200 nucleotides can be assemble in de novo SBH, and the pool size would be about $(16\times10^6)/(3200\times8)=625$ probes; the number of pools would be 25,600.

R should be chosen such that it prevents branching out and looping, where a minimal false branch must be C=K, and must start and end with a positive probe; the other options are false branching out on many sites of normal sequence. For C=10, Pc(10) (one way) 1/1000, and the number of out branching in any of the two directions of a segment of correct sequence is [2×3200]/1000=6 cases. By using length requirement and end sequence knowledge, these false sequences will be eliminated.

If all fragments assembled to about 20 cycles stop due to false negative probes (e.g., 5%), an overlap of K-2 must be used on about 200 different sites for a 3200 base target. Additional data from hybridization of an overlapping 7-mer probe will be sufficient for correct assembly in this case, and thus the algorithm will proceed with maximal overlap, then reducing by one nucleotide. Only branches longer than C can be used in further assembly to assure a small probability for false overlaps; in the K-2 step, the number of further used branches should be about 4-fold reduced compared to the number of scored K-mer probes.

The extensive occurrence of falsely scored pools of probes (either false positive or false negative) requires use of smaller pools. Experimental false positives must be included in the P/T ratio of 1/5. There may be experimental false positives because, e.g., the cumulative scores of several single mismatch and double mismatch probes may produce a strong enough signal to cause the pool to be scored as positive, and may dramatically increase the probability of scoring the sets of probes around K-2 or K-3 branch repeats.

The methods of the present invention utilizing pools of probes are particularly suited to Format 3 SBH, although the methods are useful in all formats. Format 3 SBH should be more accurate for scoring long probes because it uses two short, more discriminative probe modules and potentially adds the enzymatic specificity of ligase. Furthermore, Format 3 allows combinatorial scoring of large number of probes. In combination with the synthesis of pools for each of two modules, the synthesis of all 250 million possible 14-mers may be done in two sets of only 512 pools of 32 fixed and labeled 7-mers.

In Format 3, chips with a complete set of probes of a given (relatively short) length may be hybridized with targets and labeled pools of probes of short lengths. For example, a 6400 nucleotide target can be sequenced at a redundancy of R=20 with 7+6=13-mers using 131,072 dots: 32 chips each containing 4096 pools of four 7-mers as fixed probes interrogated with 32 pools of 128 6-mers as labeled probes. A saving of 500-fold would thus be achieved.

The pooling method also provides other specific advantages in Format 3 SBH. In particular, positive and negative fixed probe information may be used to reduce the number of false positives of combined oligonucleotide sequences. For example, 16 arrays containing 1024 5-mers probed with 16 pools of 64 labeled 5-mers and 500 nucleotide targets allow scoring of all 10-mers in about 16,000 dot scores, with each score representing 64 10-mers. However, many of the 10-mers in each of the positive pools can be removed from further consideration because the labeled 5-mers that form them have not been found positive as fixed 5-mers. A related method is discussed below.

In an alternative embodiment, the pooling method can be used in conjunction with multiplex labeling to further reduce the number of array locations (oligonucleotide spots) required and/or to further reduce the number of hybridization reactions required. Multiplexing involves using more than one distinguishable label (such as different fluorophores, chromophores, EML, or radioactive labels, or mixtures thereof) to identify the pool, thus allowing different pools to be combined in a single location in an array or to be combined in a single solution for hybridizing with an array. For example, labeling each of four pools with one of four fluorescent dyes can allow the four pools to be mixed together in a single solution for hybridizing with an array, reducing the number of hybridization reactions required by an additional factor of four. Alternatively, the same principle of pools can be applied in conjunction with, e.g., beads or molecular labels for sequencing longer DNA.

In an alternative embodiment, the pooling method may use continuous score values for all positive hybridizations, instead of ± calls. This embodiment would allow probabilities to be calculated for each fork.

Sequence assembly can also be carried out without assigning a "positive" or "negative" score to the probes (or pools of probes). In practice, this may be carried out by overlapping multiple (e.g., two or more, or three or more, or four or more, or five or more) consecutive probe sequences and calculating a cumulative score, or performing statistical analysis, for the overlapped sequence based on the scores of each of its constituent probe sequences. If all of the probes were positive probes, the sum of the scores should be very high. This method of overlapping using "continuous scoring" is advantageous because it is not possible to perfectly discriminate between the scores of full match and mismatched probes even under optimal hybridization and washing conditions. Thus, although on average the hybridization signals of full match probes are significantly different from the hybridization signals of mismatch probes, the, actual signal distributions of full match probes and mismatch probes can overlap. In conventional SBH, an optimal threshold is determined, and probes with scores above this threshold are called "positive" while probes with scores below this threshold are called "negative". Thus, some full match probes will be falsely scored as negatives. In contrast, the continuous scoring method of overlapping allows these false negative probes to be incorporated into the assembled sequence despite the fact that their scores fell below the positive threshold.

The method of overlapping using "continuous scoring" improves the accuracy of sequence assembly by using, e.g. cumulative scores of multiple overlapping probes. For example, starting from a known primer or a true positive probe, all possible combinations of N (e.g., where N is 2, 3, 4, 5 or more) overlapping probes may be assembled and the cumulative score calculated for each overlapping combination. An optimal N (number of overlapping probes for which a cumulative score is calculated) is in the range from 3 to K-2, where K is the number of bases in the probe. The overlapping combination(s) with the highest cumulative scores are carried forward to the next base extension. If the overlapping combination is the correct sequence, the constituent full match probes should have very high scores and the cumulative score should also be high. The process is then repeated for the next base extension. Statistically significant combinations or sets of combinations determine the next base. The significance level may be calculated for each base relative to the other three bases.

Exemplary statistical analyses of the hybridization scores of overlapping probes include summation, multiplication, averaging, median scores, and maximum likelihood statistical analyses. For example, for any set of 3 or more (or 4 or more, or 5 or more, etc.) overlapping probes, a median score may be calculated. Alternatively, an average score of the overlapping probes can be calculated after removing the smallest and largest score to minimize the influence of potential false negatives and experimental or pooling false positives.

In another embodiment, a maximum likelihood statistical analysis maybe applied as follows. For each probe from a group of overlapping probes, the probability that this probe is a perfectly matched probe may be calculated (e.g. from the distribution density of probes in the perfectly matched category). For other probes not in that group of overlapping probes, the probability of each probe being a specific type of mismatched probe (or any type of mismatched probe) may also be calculated. From these probabilities, a probability-that the sequence defined by the group of overlapped probes is the correct sequence may be calculated by multiplying the probabilities of each of the overlapped probes.

In addition to the statistical analysis of scores of a group of overlapping probes, statistical analysis may also be performed on cumulative scores or on median or average scores or probabilities for various groups of overlapping probes representing different sequences. For example, starting from one known sequence and using 10 overlapping probes, 1,048,576 different groups of 10 overlapping probes may be formed. Each of the four possible bases that may be the next base extension of the known starting sequence is represented with 262,144 groups. If, for example, A is the correct base, several groups (usually the correct one and some with false probes especially at the end) will have a high cumulative, average or median score. The decision on which base extension of the starting sequence is the most likely may be obtained by calculating the median or average score of some number (2-30) of groups with the highest score for each base. In this analysis one or more bases may be determined that extend the starting sequence.

For assembling longer sequences by repeated determination of a single or more base extension of the starting sequence using overlapping probes that match with the previously determined or known sequence, only selected groups (rather than all groups) of overlapping probes from the previous cycle can be used. For example, only 16 or 64 groups with the highest score for each base may be used. Because only one or a few new probes will be added, some of those groups with the highest score will most likely have the new highest statistical value. This process may significantly expedite sequence assembly because only a few hundred groups of overlapping probes, instead of over one million groups of overlapping probes, need to be tested. The other option is to extend selected groups by a few overlapping probes; this leads to testing a larger number of groups but it may give more accurate statistics.

Optionally, 2-3 independent sets of 2-3 fold larger pools maybe used for exponential reduction of false positives (0.1×0.1×0.1 for 10% false scored probes). Additionally, in some applications, it may be advantageous to have a single probe in more than one pool; however, the percentage of false negative probes may increase with this method.

The methods of the present invention utilizing pools can be used with other types of pools, such as redundant pools or binary pools. For example, in a combination of pooling and redundant pooling, two or more sets of pooled probes may be used. For each set, the probes are grouped into different pools, e.g., a probe that is grouped with one pool of probes in the first set will be grouped with a different pool of probes in the second set. Ideally, only probes that are positive in both sets are placed in the set of positive probes. Thus, although pooling false positives remain, fewer false positive probes are included in this set of positive probes used for sequence assembly. When continuous scoring is beingused, each probe maybe assigned the lowest of the two hybridization scores obtained from hybridization of the first and second sets.

Pools can be used with additional mapping information to allow assembly of longer sequences for a given probe length than specified in Table 3. In any SBH method, branch points produce ambiguities as to the ordered sequence of a fragment. In the assembly of relatively longer fragments, ambiguities may arise due to the repeated occurrence in a set of positively-scored probes of a K-1 sequence (i.e., a sequence shorter than the length of the probe). Additional mapping information may be used to order hybridization data where such ambiguities ("branch points") occur. For example, restriction mapping information can be used to map sequence subfragments.

In another embodiment, the sequence subfragments may be ordered by comparing the sequence of the subfragments to related sequences (e.g., a known sequence from a closely related species with over 80% sequence identity) and ordering the subfragments to produce a sequence that is closest to the related sequence. For example, according to Table 3, 1 5-mers should be used in order to assemble unambiguous 25 kb segments of genomic sequence. However, if additional mapping information is known, 12-mers may be used instead, resulting in 64-fold smaller pools. Although branching points will occur about every 200 bases, the assembled sequence subfragments can be mapped by matching them to known genomic sequence of a closely related species.

In yet another embodiment, primers for single pass gel sequencing through the branch points may be identified from the SBH sequence information or from known vector sequences, e.g., the flanking sequences to the vector insert site, and standard Sanger-sequencing reactions may be performed on the sample target nucleic acid. The sequence obtained from this single pass gel sequencing can be compared to the subfragments that read into and out of the branch points to identify the order of the subfragments.

Alternatively, the information needed to solve branching ambiguities may be directly provided by using a known reference gene sequence when assembling gene sequences from individual patient samples. When a reference sequence is known, the maximal read length in bases may be extended to approximately one tenth the number of probes used. To sequence human and other complex genomes (over 3 billion base pairs) as a single sample, about 70 billion 1 8-mer probes would be needed.

In addition, the number of tandem repetitive nucleic acid segments in a target fragment may be determined by single-pass gel sequencing. As tandem repeats occur rarely in protein-encoding portions of a gene, the gel-sequencing step will be performed only when one of these noncoding regions is identified as being of particular interest (e.g., if it is an important regulatory region).

h. Exemplary Sequence Assembly Algorithm

The following sequencing algorithm is one way in which all nucleotide sequences consistent with a set of positive probes (PP) can be assembled. If the PP is obtained using pools, the PP set may optionally be "filtered" (as described below in Section i) or optionally "rescored" as described below, or both, before being used as the input PP set. A nucleotide sequence consistent with the input set of PP is composed for the most part of probe sequences from the PP. However, because false negatives are expected to occur, extension of assembled sequence must be allowed even if some probe sequences are "missing" from the PP in order to guarantee that the correct nucleotide sequence will be among the putative sequences generated.

In one exemplary embodiment, the sequencing algorithm can commence after the following fixed input parameters have been specified: a known 9 base primer (from which sequence assembly starts), a "cleaned" (or filtered) set of PP obtained as described immediately below, and preset parameters specifying the approximate length of the target nucleic acid sequence (MaxLength) and how many missed probe sequences (MaxMisses) and consecutive missed probe sequences (MaxConsecutiveMisses) can be allowed while sequencing (thus allowing, e.g., K-2 or K-3 overlapping of probe sequences despite some expected false negatives). MaxMisses may range from 1% to 10% but is preferably set to 5%. Even for modest values of MaxMisses (e.g., 8), the overwhelming majority of assembled sequences with that number of misses turn out to be incorrect. MaxConsecutiveMisses may range from 1 to 3 but is preferably set to 2. The MaxLength may be a fixed number or a range of numbers. For example, assembly of sequence from 5' to 3' can be done as follows:

1) At each position i (in this case meaning the i-th position after the primer sequence), the following 4 variables are updated:
   - (a) suffix9: the 9 consecutive bases before the current position i (i.e., the last 9 bases of the sequence that has been assembled so far);
   - (b) #misses: the total number of "misses" (missing probe sequences) within the sequence assembled so far;
   - (c) #cmisses: the number of consecutive misses (consecutive missing probe sequences) at the end of the sequence assembled so far.
   - (d) length (L): the length of the sequence assembled so far—9 (nine is subtracted because the sequence started with a known 9-base primer)
2) When sequence assembly commences, initially the variables are set to:
   i=1, suffix9=primer, #misses=0, #cmisses=0, L=0.
3) One base (one of A, C, G, or T) is temporarily added to the 3' end of suffix9 to make a 10-mer sequence. For convenience, this added base is referred to as "X", and the 10-mer created by addition of X to the end of suffix9 is denoted as "suffix9X".
4) X is added to the 3' end of the assembled putative sequence if suffix9X is in the PP set. Alternatively, X may be added to the 3' end of the putative sequence as a base from a missing (i.e. false negative) probe (the correctness of X can be verified with a later overlapping positive probe), provided that the total number of misses accumulated thus far in the sequence is less than the preset parameter MaxMisses, and the number of consecutive misses at the 3' end of the sequence is less than the preset parameter MaxConsecutiveMisses. This can be carried out as follows:
   - (a) If the sequence for suffix9X is in the PP, and if L<Maxlength−9, X is added to the assembled sequence. (If L=Maxlength−9; then sequence assembly stops). Suffix9 is now updated to be the last 9 bases of suffix9X; L=L+1 (L is incremented by 1); #misses=#misses (# misses stays the same); and #cmisses=#cmisses (#cmisses stays the same).
   - (b) If suffix9X is not in the PP, if #misses<maxMisses, if #cmisses<MaxConsecutiveMisses, and if L<maxLength−9, then X is added to the assembled sequence. Suffix9 is now updated to be the last 9 bases of suffix9X; L=L+1; #misses=#misses+1 (#misses is incremented by 1); #cmisses=#cmisses+1 (#cmisses is incremented by 1)
5) Steps 3 and 4 are repeated until the #misses reaches the MaxMisses, or until the #cmisses reaches the MaxConsecutiveMisses, or until sequencing stops (when L reaches Maxlength−9).

At any i-th position, two or more possible "suffix9X"s may be present in the PP (particularly when pools are used). For example, suffix9X where X is A may be present in the PP and suffix9X where X is T may also be present in the PP. Both sequences would be held in memory as possible assembled sequences. In addition, when a missed probe is being allowed at an i-th position, X may be any one of A, C, G or T, so all four possible assembled sequences would be held in memory. Thus, multiple assembled sequences are typically kept in memory as "branching" possibilities until they are eliminated because they include too many missed probes. Each possible sequence can be called a node on a tree or graph. It is possible that multiple sequences can successfully assemble to the maxLength without violating the MaxMisses or MaxConsecutiveMisses limits; in this case, there will be multiple final putative assembled sequences. To reduce memory requirements, it is worthwhile to prune away useless nodes that can be shown not to lead to a node of MaxLength. Generally, this pruning method involves determining whether a node of length L leads eventually to a node of MaxLength; if not, then it is removed. The eliminated node's predecessors are also examined and are pruned if they lead to no other nodes except the node that was just eliminated. By applying this pruning recursively, all nodes that do not lead to a node of MaxLength are eliminated.

6) Each final putative assembled sequence is rechecked from 3' to 5'. Starting with the last position in the assembled sequence, the first base of the probe at the previous position is attached to the 5' end and the presence of this newly created 10-mer in the PP is checked. Typically, repeated 10-mers are excluded during this rechecking step, i.e. putative sequences are eliminated if the presence of the new 5'base would create a 10-mer that had already been "counted" as included in the assembled sequence.

i. Filtering Out False Positives

In order to reduce the computational requirements of the sequence assembly process described above, false positives may optionally be filtered by first overlapping sequences of small numbers of positive probes prior to assembling sequences of all of the positive probes into the complete putative target sequence. Each positive probe is overlapped with a small number (ranging from, e.g., K/2 to 2K) of other positive probes to provide an extended sequence in either direction, and only the extendible probes are kept in the set of positive probes that will be used to form the complete sequence.

The filtering algorithm removes false positives generated from any of the three most significant sources of false positives, i.e., single nucleotide mismatches, single nucleotide insertions, and single nucleotide deletions, as well as false positives due to target-independent probe-probe ligation. Filtering is particularly advantageous for SBH methods using pools of probes, because of the very high number of false positives generated by these methods.

In one embodiment, the set of positive probes (PP), e.g. 10-mers, which initially contains all probes in the positive pools may be "cleaned" by keeping only extendable probes (i.e., probes that overlap with other positive probes) in the set of all PPs, as follows:

1) Starting with the initial PP set, determine all possible 18-mers that can be constructed by overlapping 9 consecutive hypothetical 10-mers in the PP set. An exemplary 18-mer overlap is shown below:

```
GGTCTcccca          1    (SEQ ID NO:7)
 GTCTCcccaa         2    (SEQ ID NO:8)
  TCTCCccaag        3    (SEQ ID NO:9)
   CTCCCcaagg       4    (SEQ ID NO:10)
    TCCCCaaggc      5    (SEQ ID NO:11)
     CCCCAaggcg     6    (SEQ ID NO:12)
      CCCAAggcgc    7    (SEQ ID NO:13)
       CCAAGgcgca   8    (SEQ ID NO:14)
        CAAGGcgcac  9    (SEQ ID NO:15)
```

2) Only those 10-mers that appear as the middle 10-mer of one of these 18-mers (i.e. the fifth 10-mer among the 9 overlapped 10-mers) and that were originally in the PP set are kept in the PP set.

3) In alternative embodiments, the stringent requirement that there be 9 consecutive 10-mers may be relaxed by allowing overlap despite 1 or 2 missing 10-mer probes. For example, one can allow the 18-mers to be assembled from, e.g., 7 or 8 non-consecutive 10-mers.

i. Exemplary Filtering Algorithm for Format 3

Use of pooling methods in Format 3 SBH provides special advantages in the sequence assembly process. False positive results can be eliminated, or at least greatly reduced, by using a filtering algorithm to build a set of "clean" positive K-mers, based on combining the information from the fixed probes and the labeled solution probes. The filtering algorithm may be performed by hand, but the quantity of data generated makes it preferable to perform it using a computer as described in detail below. The basic thrust of the filtering algorithm is to use the information from all overlapping probes to verify each position in a given K-mer. When each position is verified, the resulting K-mer is declared "clean" and is then stored in a table for subsequent input into the K-mer sequence assembly algorithm. The method for eliminating false positives is here exemplified in terms of using the information from 5-mer fixed probes and 5-mer labeled solution probes to generate clean 10-mers; however, one of skill in the art will recognize immediately that the same filtering algorithm can be easily adapted for fixed and solution probes of other lengths to generate clean K-mers of any desired length.

In the following illustration, the filtering algorithm is applied to data generated from 16 oligonucleotide pools, each containing 64 labeled 5-mer probes, that are used in conjunction with 16 different oligonucleotide arrays, each of which contains the complete set of 1024 fixed 5-mer probes in a spatially addressable array. Each possible 5-mer is present in one and only one pool, and the pools are constructed according the criteria discussed above. The labeled pools of probes are ligated to the fixed probes in the presence of a target nucleic acid, following standard SBH Format 3 protocols, and the signal of each spot on each array is read. Control arrays without the target nucleic acid are probed in parallel. A "dirty" table of positive 5-mers is built by subtracting the control signals from the target signals, and taking as positive those above a selected threshold value. This initial table of 5-mers is based solely on the fixed probes, and ignores the sequences of the pooled probes. The table potentially contains at least some false positive 5-mers, in addition to correct 5-mers.

(a) For each of the positive 5-mer probes, the standard K-mer sequence assembly algorithm is used to extend the sequence for 5 nucleotides at the 3' end. For example, if a portion of a (theoretical) nucleic acid has a sequence complementary to

```
TGCTT GCCAC AGGTC TCCCC AAGGC GCACT  (SEQ ID NO:16)
```

then the probe AGGTC should be positive. Extending the sequence 5 nucleotides using K-1=4 nucleotide overlaps generates the 10-nucleotide sequence:

```
AGGTCtcccc           (SEQ ID NO:17)
 GGTCTcccca     1    (SEQ ID NO:18)
  GTCTCcccaa    2    (SEQ ID NO:19)
   TCTCCccaag   3    (SEQ ID NO:20)
    CTCCCcaagg  4    (SEQ ID NO:21)
     TCCCCaaggc 5    (SEQ ID NO:22)
```

(b) If this is the correct extension, then the labeling probe for the fixed AGGTC probe should be tcccc. The pool that gave the positive signal for AGGTC is then checked to see if it includes tcccc. If not, the generated 10-mer is discarded as presumably incorrect, and step (a) is repeated with a different alignment of the starting 5-mer or with a different 5-mer. If the pool does contain the extended sequence, the generated 1-mer is further analyzed.

Note that the analysis, here and below, discusses checking only one pool for a positive signal. However, it is possible (indeed probable) that repeated 5-mers in the sequence will cause at least a few fixed probes to be positive with more than one labeled pool. This does not affect the analysis, which checks only that the fixed 5-mer is positive with the correct pool; it does not require that it be uniquely positive with that pool. Thus, the present discussion ignores these other positive pools as irrelevant. When used on the complete data set, the filtering algorithm will analyze all of the possible extensions of each positive fixed 5-mer, and thus all correct positives will eventually be verified and placed in the clean 10-mer table.

(c) The 5-mer table is then used to align forward for a sixth nucleotide, generating:

```
AGGTCtcccc              (SEQ ID NO:17)
 GGTCTcccca       1     (SEQ ID NO:18)
  GTCTCcccaa      2     (SEQ ID NO:19)
   TCTCCccaag     3     (SEQ ID NO:20)
    CTCCCcaagg    4     (SEQ ID NO:21)
     TCCCCaaggc   5     (SEQ ID NO:22)
      CCCCAaggcg  6     (SEQ ID NO:23)
```

Again the data are checked to see that cccca is in the pool that generated the signal for fixed probe GGTCT. If so, the filtering algorithm continues; if not, the filtering algorithm is started again at step (a) with a new alignment or a new 5-mer.

(d) The verification is then repeated for all probes up through a total of 5 nucleotides beyond the starting 5-mer (which requires reading 9 nucleotides beyond the starting 5-mer), generating

```
AGGTCtcccc                 (SEQ ID NO:17)
 GGTCTcccca          1     (SEQ ID NO:18)
  GTCTCcccaa         2     (SEQ ID NO:19)
   TCTCCccaag        3     (SEQ ID NO:20)
    CTCCCcaagg       4     (SEQ ID NO:21)
     TCCCCaaggc      5     (SEQ ID NO:22)
      CCCCAaggcg     6     (SEQ ID NO:23)
       CCCAAggcgc    7     (SEQ ID NO:24)
        CCAAGgcgca   8     (SEQ ID NO:25)
         CAAGGcgcac  9     (SEQ ID NO:26)
```

(e) Through this iterative process, each nucleotide in the second half of the 10-mer has been verified. If each step is positive, the next step is to work backwards and repeat the steps of using 4-nucleotide overlaps from the 5-mer table to determine the preceding sequence and then to verify the presence of the 5-mer in the pool generating the signal for the positive 5-mer:

```
CAGGTctccc            1     (SEQ ID NO:27)
 AGGTCtcccc                 (SEQ ID NO:17)
  GGTCTcccca          1     (SEQ ID NO:18)
   GTCTCcccaa         2     (SEQ ID NO:19)
    TCTCCccaag        3     (SEQ ID NO:20)
     CTCCCcaagg       4     (SEQ ID NO:21)
      TCCCCaaggc      5     (SEQ ID NO:22)
       CCCCAaggcg     6     (SEQ ID NO:23)
        CCCAAggcgc    7     (SEQ ID NO:24)
         CCAAGgcgca   8     (SEQ ID NO:25)
          CAAGGcgcac  9     (SEQ ID NO:26)
```

Again, the data are checked to see that the labeling probe ctccc is in the pool that gave a signal with fixed probe CAGGT. If so, the filtering algorithm continues with the next step; if not, it starts again at (a) with a new alignment or a new starting probe.

(f) The verification is next repeated backward through a total of 9 steps:

```
GCTTGccaca                        9 (SEQ ID NO:28)
 CTTGCcacag                       8 (SEQ ID NO:29)
  TTGCCacagg                      7 (SEQ ID NO:30)
   TGCCAcaggt                     6 (SEQ ID NO:31)
    GCCACaggtc                    5 (SEQ ID NO:32)
     CCACAggtct                   4 (SEQ ID NO:33)
      CACAGgtctc                  3 (SEQ ID NO:34)
       ACAGGtctcc                 2 (SEQ ID NO:35)
        CAGGTctccc                1 (SEQ ID NO:27)
         AGGTCtcccc                 (SEQ ID NO:17)
          GGTCTcccca              1 (SEQ ID NO:18)
           GTCTCcccaa             2 (SEQ ID NO:19)
            TCTCCccaag            3 (SEQ ID NO:20)
             CTCCCcaagg           4 (SEQ ID NO:21)
              TCCCCaaggc          5 (SEQ ID NO:22)
               CCCCAaggcg         6 (SEQ ID NO:23)
                CCCAAggcgc        7 (SEQ ID NO:24)
                 CCAAGgcgca       8 (SEQ ID NO:25)
                  CAAGGcgcac      9 (SEQ ID NO:26)
```

If all labeling probes are permissible (i.e., the fixed probe is positive with the correct pool), then the 10-mer AGGTGtcccc is put into the clean 10-mer table. Preferably, if any of the predicted probes are found not to be correct, then AGGTGtcccc is not put into the table. Use of the filtering algorithm results in each position in the 10-mer being verified by 10 overlapping probes before it is added to the clean 10-mer table. In certain situations, however, such as when the data contains many false positives, it may be preferable to rely on a threshold number of permissible probes, preferably at least about 50%, more preferably at least about 75%, and especially preferably at least about 90%.

The resulting final clean 10-mer table should contain all true 10-mers, as long as the data contain no false negatives. Once the table of clean 10-mers has been generated, the K-mer sequence assembly algorithm is used to assemble the 10-mers into the complete sequence of the target DNA. As will be apparent from review of the above filtering algorithm, however, it cannot be fully extended to cover the starting and ending nucleotides. Therefore, the first 9 and the last 9 nucleotides are given special treatment. For the first 9 nucleotides, the basic filtering algorithm is repeated, working backward. As much data as possible is generated for each nucleotide in the sequence; however, each earlier nucleotide is less completely verified than the following nucleotide. Thus, the 9th nucleotide is read only 9 times, the 8th nucleotide only 8 times, and so on. The first nucleotide is read only once. It is identified by comparing the ligation signals for the four 10-mers that overlap nucleotides 2-10 and vary only at position 1. The one with the highest signal is chosen as the correct first nucleotide. For the example sequence, positions 2-10 are determined to be GCTTGCCAC. The signals for AGCTTGCCAC (SEQ ID NO:36), TGCTTGCCAC (SEQ ID NO:37), CGCTTGCCAC(SEQ ID NO:38), and GGCTTGCCAC (SEQ ID NO:39) are compared, and the strongest signal (which should be TGCTTGCCAC (SEQ ID NO:37)) is used to determine the first nucleotide. A similar approach is applied to the last 9 nucleotides, proceeding in the forward direction. In addition, the last nine positions can be further checked using only the sequence of the fixed 5-mer probes (ignoring the pooled solution probes), thus strengthening the determination of these positions.

ii. Computing Device for Filtering

Figure 2:
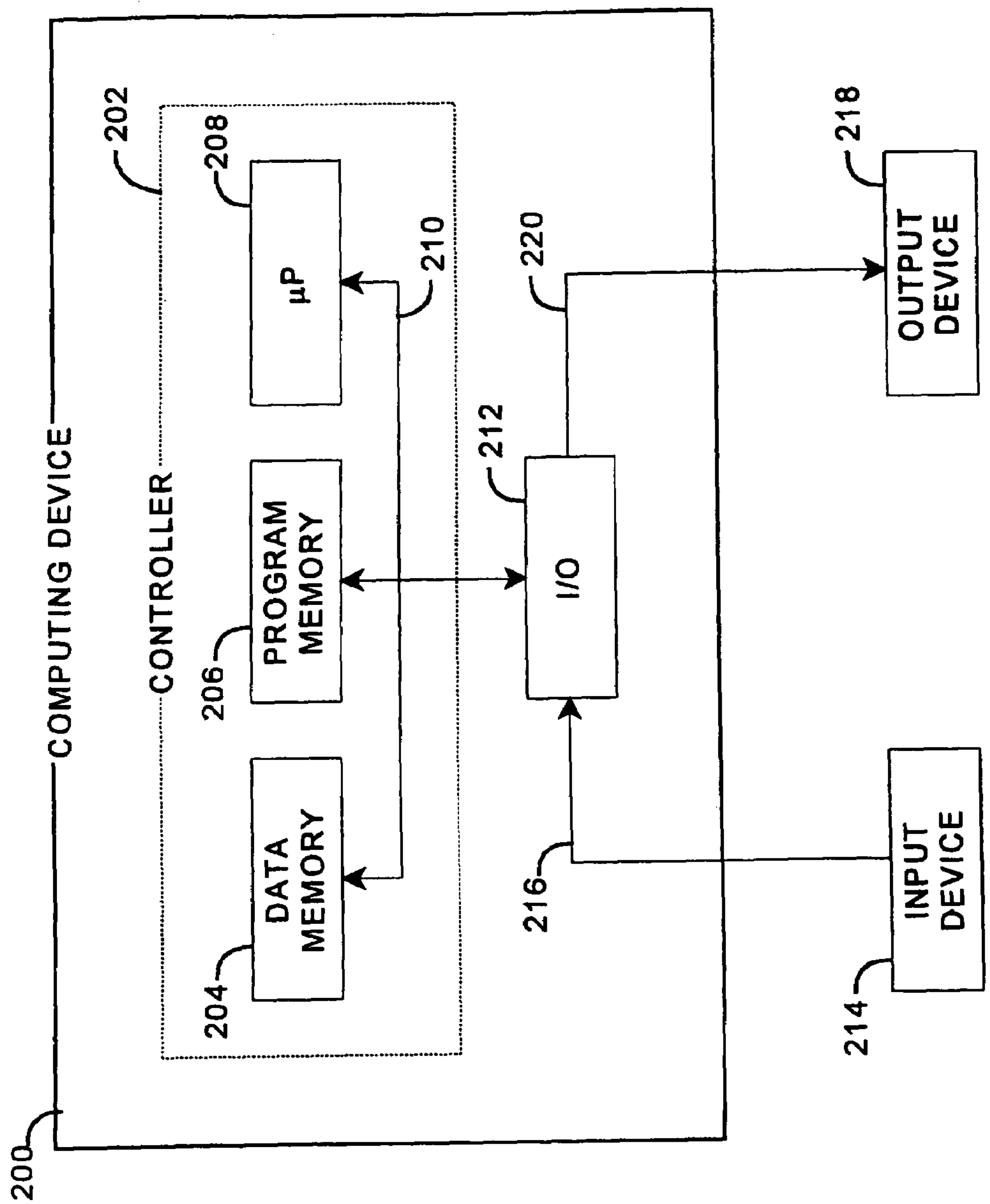
FIG. 2 is diagram of a computing device.

A diagram of a nucleic acid sequencing system including a computing device 200 capable of implementing the teachings of the present invention is illustrated in FIG. 2. The computing device 200 may be a general purpose computer programmed to implement the method and/or apparatus of the present invention, or the computing device 200 may be an application specific device designed to implement the method and/or apparatus of the present invention as is well known to persons of ordinary skill in the art. A controller 202 in the computing device 200 may include a data memory 204, such as a random-access memory and/or a disk drive, a program memory 206, which may be in the form of a read-only memory (ROM), and a microprocessor 208, all of which may be interconnected by an address/data bus 210. In one embodiment, the program memory 206 electronically stores a computer program that implements all or part of the method described below, and the program is executed by the microprocessor 208. The program memory 206 may be loaded from a fixed memory device such as a hard drive, or the program memory 206 may be preloaded with firmware as is well known to persons of ordinary skill in the art. Some of the steps described in the method below may be performed manually or without the use of the computing device 200.

A transmitter and receiver in the form of a conventional input/output (I/O) circuit 212, such as a modem for example, typically couples the controller 200 to external devices. An input device 214 such as a keyboard, mouse, and/or optical scanner may be connected to the I/O circuit 212 via a line 216 for entering data and commands into the controller 202. Further, an output device 218, such as a display or printer, may be connected to the I/O circuit 212 to receive data via a line 220 to generate visual displays of data generated during operation of the computing device 200.

Figure 3:
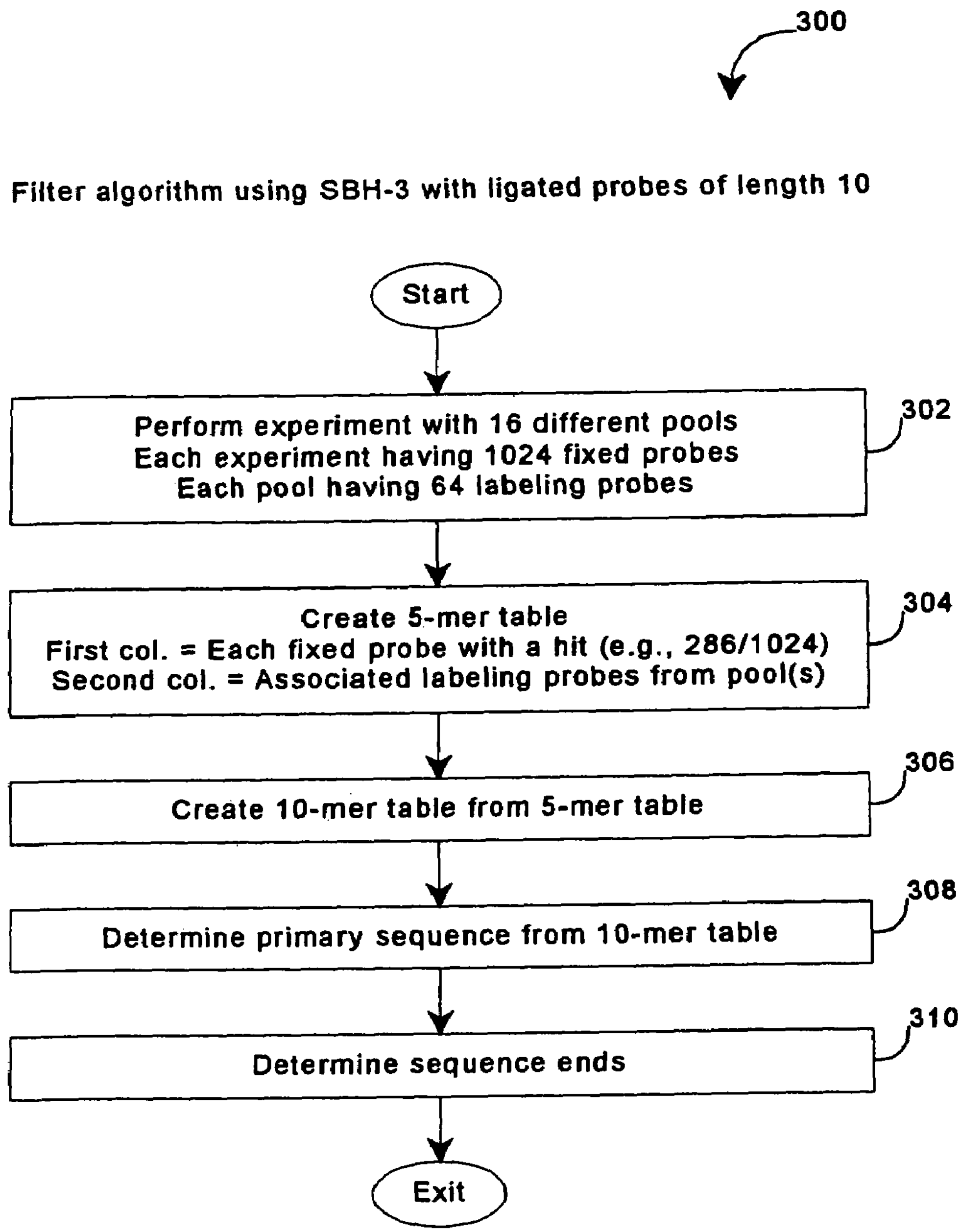
FIG. 3 is a flow chart describing an algorithm to filter out false positive probes in a set of probes.

A flowchart of one possible process 300 of nucleic acid sequencing by hybridization using pools of probes is illustrated in FIG. 3. The process 300 can be implemented by a human operator and/or the computing device 200 in accordance with the teachings of the present invention. In one embodiment, the programmed steps performed by the computing device 200 are executed by the controller 202. Generally, the process 300 employs a complete set of fixed probes in conjunction with a complete set of labeling probes. However, the labeling probes are combined into a relatively small number of pools. Ligation information from a reduced number of experiments is then processed to determine a target sequence.

When the process 300 is initiated, a researcher and/or an automated testing apparatus performs a sequencing by hybridization Format 3 experiment for each of the pools of labeling probes (step 302). In this example, the fixed probes are 5-mers and the labeling probes are 5-mers. Accordingly, each experiment contains 1024 fixed probes and 1024 labeling probes (i.e., $4^5$). Of course, a person of ordinary skill in the art will readily appreciate that any number of fixed probes and any number of labeling probes may-be used in the scope and spirit of the present invention. Further, in this example, sixteen pools of probes with sixty-four labeling probes per pool are used. However, it is understood that any number of pools may be used. Still further, a person of ordinary skill in the art will readily appreciate that SBH Format 1 and/or SBH Format 2 could also be used in the scope and spirit of the present invention.

When all sixteen experiments are completed, a certain number of fixed probes will indicate that a ligation has occurred (e.g., 286 of the 1024 fixed probes fluoresce). Certain fixed probes may "hit" (i.e., display a true signal) when the first pool of labeling probes is used. Other fixed probes may "hit" when the second pool of labeling probes is used, and so on through all sixteen pools of labeling probes. However, at this point in the process 300 it is unknown which of the sixty-four labeling probes in a particular pool actually caused the ligation to occur.

At step 304, a 5-mer table is preferably created. The 5-mer table documents the results of the experiment by placing each fixed probe with a true signal in a first column (e.g., "CTCGA") and the associated labeling probes in a second column (e.g., "pool 7" or "TCCGG, GTCTC, CGTTC, . . . "). Of course, any data structure may be used for this purpose. In this example, if a particular fixed probe is associated with one pool, there will be sixty-four labeling probes in the second column. If a particular fixed probe is associated with two pools, there will be 128 labeling probes in the second column etc.

Once the 5-mer table is created, a O-mer table is determined from the 5-mer table at step 306 (described in detail below). Of course, a person of ordinary skill in the art will readily appreciate that a table of any size oligomers (e.g., 15-mers) may be created using the teachings of the present invention. Subsequently, a primary sequence is determined form the 10-mer table at step 308 in a known manner. The sequence ends are treated separately at step 310.

Figure 4:
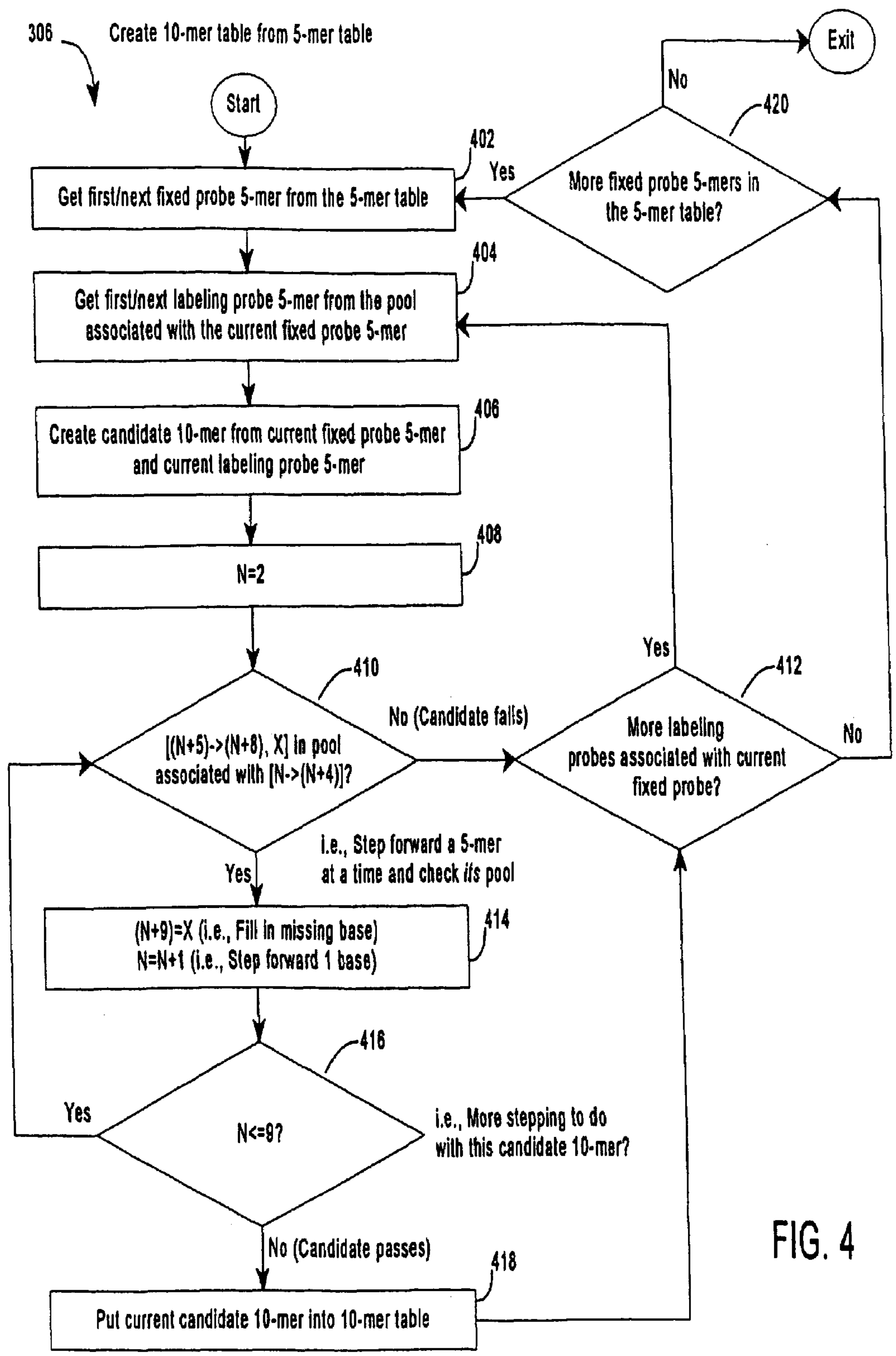
FIG. 4 shows a flow chart for sequence analysis using Format 3.

One way of implementing process 306 to determine the 10-mer table from the 5-mer table (shown schematically in FIG. 3) in accordance with the teachings of the present invention is illustrated in the flowchart of FIG. 4. Many other methods, of arranging similar steps may also be used to achieve the same result of determining the 10-mer table from the 5-mer table. In one embodiment, the steps are performed by an human operator and the controller 202. The process 306 begins at step 402 by retrieving the first fixed probe 5-mer from the 5-mer table created in step 304. Subsequently, at step 404, the process 306 also retrieves the first labeling probe 5-mer from the pool associated with the current fixed probe 5-mer (e.g., the first possible match out of sixty-four labeling probes in the pool). The fixed probe 5-mer and the labeling probe 5-mer are then combined into a candidate 10-mer at step 406.

The candidate 10-mer is then tested against the other data acquired to determine if should be placed in the 10-mer table or discarded. At step 408, an index variable is initialized to "2" in order to point to the 5-mer starting one base in from the end of the candidate 10-mer. For example, if the candidate 10-mer is "CTCGATCCGG" (SEQ ID NO:40), the 5-mer defined by [N→(N+4)] is "TCGAT" (i.e., CTCGATCCGG (SEQ ID NO:40)). Similarly, when N=2, the 5-mer defined by [(N+5)→(N+8), X] is "CCGGX" where X is unknown at this point in the process (CTCGATCCGG). The "question" for the data is whether the 9-mer "TCGATCCGG" makes sense and, if so, what is the value of X?

In order to answer these questions, the process 306 looks in the pool associated with the fixed probe 5-mer "TCGAT" for a labeling probe that starts out with "CCGG" at step 410. If a labeling probe starting with "CCGG" is not found in the pool associated with the fixed probe "TCGAT", then the process 306 discards this candidate 10-mer (i.e. the process 306 does not store this 10-mer in the 10-mer table). In such an instance, the process 306 determines if there are more labeling probes associated with the current fixed probe at step 412. If there are more labeling probes to test, the process 306 loops back to step 404 to retrieve the next labeling probe from the associated pool and the process repeats. In other words, if the process 306 just tested the first labeling probe of sixty-four possible labeling probes, then it moves on to the second labeling probe.

In this example, if a labeling probe starting with "CCGG" is found in the pool associated with the fixed probe "TCGAT" at step 410, then the process 306 extends the 10-mer by tacking X onto the end of the candidate 10-mer and steps forward one base at step 414. X is determined to be the fifth base in the labeling probe starting with "CCGG". If more than one labeling probe starting with "CCGG" is found, the process may "fork" until a failure is found, thereby eliminating all but one of the labeling probes.

The process 306 in this example preferably steps forward until the candidate 10-mer fails (see "No" branch of step 410) or nine forward steps have been successfully completed as determined by testing N at step 416. If nine forward steps are successfully completed, the process 306 stores the candidate 10-mer in the 10-mer table at step 418. Of course, a person of ordinary skill in the art will readily appreciate that any number of forward steps may be used as a threshold for storage of a candidate 10-mer in the 10-mer table. Further, any number of reverse steps may be performed in a similar manner.

When all of the labeling probes associated with a particular fixed probe have been tested, the process 306 determines if there are more fixed probes in the 5-mer table at step 420. If there are more fixed probes to test, the process 306 loops back to step 402 to retrieve the next fixed probe from the 5-mer table and the process repeats. In other words, if the process 306 just tested the first fixed probe with a true signal, then it moves on to the second fixed probe with a true signal. When all fixed probes and associated labeling probes have been combined into candidate 10-mers and tested, the 10-mer table is complete, and the process 306 exits. Candidate 10-mers can also be tested in parallel rather than sequentially.

j. Rescoring: Allowing Mismatched Probes to Vote for Full Match Probes

SBH sequence assembly may be improved by optional score recalculation methods that involve assigning a new score (or a "rescore") to each probe by analyzing scores of probes which are one or two bases different (i.e., have a single mismatch or a double mismatch compared to the probe of interest). This is especially advantageous when pools of probes are used because otherwise each of the probes in a pool are assigned the same score. For example, score recalculation using scores of single mismatch probes may be carried out in format 3 SBH utilizing 10-mer probes by determining a value "P" as follows:

1) First, for each 10-mer probe (designated, e.g., probe X), a value "S" is calculated.
   (a) At each position "i" of probe X (e.g., i maybe 0 through 9), scores of the four probes that could vary at this position (i.e., probe X and the three possible single mismatch probes at position i) are examined and the standard deviation S(i) of the four scores is calculated.
   (b) S =max[S(i)] as i ranges from 0 to 9 (i.e., S is set to be the largest of the 10 standard deviations S(i) obtained in step 1(a)).
2) Next, for each probe X, the P value is calculated from the original score and S as determined in step 1:
   (a) Slope=(the original score of X)/(S for X)
   (b) P=1.0/abs (Slope−2). The slope will be very close to 2 for a full match probe, so P will be very high for a full match probe.

Although S itself could be used as a rescore (S should be very high if X is a full match probe), preferably the P value is used as the rescore.

Alternatively, scores of single mismatch and double mismatch probe can be taken into account by calculating a rank R for the probe X as follows. The P values for a set consisting of: X, all of X's 30 single mismatches, and all of X's 405 double mismatches are examined. The 436 probes in this set are sorted by their P values. R (also called the slope-rank) is then set to be the rank of X among the 436 probes after this sort has taken place. If X is a full match probe, it is expected to be the highest ranked (where, e.g., number 436 is the highest ranked). R may then be used as the rescore.

Yet a third alternative for recalculating the score of probe X involves calculating the sum of the scores of the 6 overlapping 5-mers that constitute the sequence of probe X. For example:

1) For each 5-mer, a "Y" value is determined where Y is the sum of the original scores of all probes or all pools of probes in which the 5-mer was the fixed probe. For example, if 16 pools were used, Y is the sum of all 16 pool scores in which that 5-mer was the fixed probe.
2) Each 10-mer (probe X) gets a score based on the sum of the Y values of its 6 overlapping constituent 5-mers. If X is a full match probe, each of the 6 scores should be large, since each of the constituent 5-mer should itself have hybridized to target as part of another 10-mer. The sum of the Ys can then be used as a the rescore of X.

Rescoring, although optional, is advantageous for determining sequence using pools. For example, rescoring allows removal of 50-80% of positive 10-mer probes from the initial PP without causing false negatives. Rescoring may also be used as an improvement to other known SBH methods, including conventional format 1, 2 or 3 SBH, to provide better discrimination between full match probes and mismatch probes than is provided by the original scores based on hybridization intensity signals.

k. Determining Likelihood Scores for Probes or Assembled Sequences

SBH sequence assembly methods can also be improved by employing a method for determining the likelihood, or probability, that a putative (or candidate) nucleotide sequence, consisting of overlapping sequences of informative regions of probes, is the correct nucleotide sequence of the target nucleic acid.

For each putative nucleotide sequence, the probes (or pools of probes) are divided into two or more categories, e.g., full match probes, single mismatch probes, single mismatch probes where the mismatch occurs at the labeling end, G/T mismatched probes, etc. The probes or pools of probes are placed in a category by assuming that the putative nucleotide sequence is correct and comparing the putative sequence to the probe sequence. When only two categories are used, probes are placed in either the full match or the mismatch category.

For each category of probes, the hybridization signal intensity for each probe (or pool of probes) in that category is plotted as a distribution density, e.g., the x-axis is intensity value and the y-axis is the relative frequency (density) of that intensity value within that category. In a rough approximation, for example, the intensity values could be divided into small intervals and the frequency for each interval could be calculated. Each probe (or pool of probes) within the category is then assigned a probability value that is equal to the density value corresponding to the probe's intensity value. For example, if a probe is in the full match category and had an intensity value of 10,000, and if 10 probes in the full match category had an intensity of 10,000-11,000, then the probability value for this probe is 10 divided by the total number of probes in that category.

After each probe (or pool of probes) has been assigned a probability value, the multiplication product of probability values for all of the probes (or pools of probes) is determined (i.e., the values-are all multiplied together). This multiplication product is now the "likelihood" of the putative nucleotide sequence, and the sequence with the maximum likelihood has the highest probability of being the correct sequence.

l. Sequencing Applications Using Pools of Probes

Although discussed in terms of de novo sequencing, one of skill in the art will recognize that the pooling method can be used for sequencing even longer targets, if they are similar (preferably >95% similar) to known reference sequences. Specific pools may be used to generate clones or DNA fragment signatures, recognize sequences, score known POLYMORPHISMS and perform others types of DNA sequence analyses.

The pooling method is also advantageous in sequencing 50-150 kb bacterial artificial chromosomes (BACs) and other long clones, using 16-17-mer probes. Such a method would preferably utilize about one million pools with 4000-16,000 probes per pool. Pools with these high numbers of probes would require higher sensitivity of detection and more efficient high density arrays. With Format 3, the one million pools can be prepared by synthesis of 1000 fixed pools of 8-mers or 9-mers and 1000 labeled pools of 8-mers, each having about 100 probes. Alternatively, other combinations, such as 10,000 fixed and only 100 labeled pools, may be used. For preparing the large pools, smaller pools may be synthesized and then pools of pools prepared. Additionally, the availability of a reference sequence from a similar species may allow sequencing of long clones with shorter probes, such as 12-mers, using 250,000-500,000 pools containing 32-64 probes, without the need for PCR. This example demonstrates particular advantages of pools in dealing with large number of long probes and long targets.

The sequence information obtained may be applied to the efficient identification and sequencing, including resequencing, of one or more nucleic acid samples. The procedure has many applications in nucleic acid diagnostics, forensics, and gene mapping. It also may be used to discover mutations and POLYMORPHISMS including single nucleotide POLYMORPHISMS (SNP) in a selected portion of a gene, the full gene, the entire genome, or a subset of the genome, to identify mutations responsible for genetic disorders and other traits, to verify the identity of nucleic acid fragments, to identify infectious agents, specific strains thereof, or mutants thereof (including viruses, bacteria, fungi, and parasites), to identify nucleic acid in samples for forensic purposes or for parental identification, to assess biodiversity and to produce many other types of data dependent on nucleic acid sequence. See, e.g., Examples 19 through 27 of Int'l Publication No. WO 98/31836 published Jul. 23, 1998 and WO 99/09217 published Feb. 28, 1999, both of which are incorporated herein by reference.

In addition, obtaining information about the degree of hybridization exhibited for a set of only about 200 oligonucleotides probes (about 5% of the effort required for complete sequencing) defines a unique signature of each gene and may be used for sorting the cDNAs from a library to determine if the library contains multiple copies of the same gene. By such signatures, identical, similar and different cDNAs can be distinguished and inventoried. See, e.g., Example 34 of WO 99/09217 published Feb. 28, 1999, incorporated herein by reference.

With improved engineering of miniaturized devices, appropriate resolution and sensitivity for detecting hybridization signals, appropriate specificity in discriminating full match probes from mismatched probes, and use of pools with multiplex labeling, whole bacterial artificial chromosomes (or even bacterial genomes using 15-mers and providing mapping information for 1 kb subfragments) may be routinely de novo sequenced in one reaction.

A specific hybridization scoring method may be employed to define the presence of mutants in a genomic segment to be sequenced from a diploid chromosomal set. Two variations are where: i) the sequence from one chromosome represents a known allele and the sequence from the other represents a new mutant; or, ii) both chromosomes contain new, but different mutants. In both cases, the scanning step designed to map changes gives a maximal signal difference of two-fold at the mutant position. Further, the method can be used to identify which alleles of a gene are carried by an individual and whether the individual is homozygous or heterozygous for that gene.

Scoring two-fold signal differences required in the first case may be achieved efficiently by comparing corresponding signals with homozygous and heterozygous controls. This approach allows determination of a relative reduction in the hybridization signal for each particular probe in a given sample. This is significant because hybridization efficiency may vary more than two-fold for a particular probe hybridized with different nucleic acid fragments having the same full match target. In addition, different mutant sites may affect more than one probe depending upon the number of probes. Decrease of the signal for two to four consecutive probes produces a more significant indication of a mutant site. Results may be checked by testing with small sets of selected probes among which one or few probes selected to give a full match signal which is on average eight-fold stronger than the signals coming from mismatch-containing duplexes.

i. Exemplary Mutation Identification Algorithm Using Likelihood Scores

The likelihood score provided by the algorithm described above, which determines the probability that a putative nucleotide sequence is correct, may also be utilized as follows to identify mutations in a gene. For each base at position i within a reference gene sequence, there are 7 possible mutations (total of 8 sequence variants including the reference sequence): 3 possible substitutes, 3 possible insertions, and a possible deletion. For example, if the reference sequence is CGT, at the second position the "G" may be substituted with an A, C or T (giving rise to the sequences CAT, CCT or CTT, respectively), there maybe an insertion of A, C, T or G before the G (giving rise to the sequences CAGT, CCGT, CTGT or CGGT, respectively), or the G may be deleted entirely (giving rise to the sequence CT).

In one exemplary embodiment, the mutation identification algorithm may be carried out using the following preset parameters which were empirically determined: threshold 1 (typically 0.995) and threshold 2 (typically 0.999).

1) For each position "i", the likelihood of the reference sequence and the likelihood of each of the 7 possible mutations at the i position are examined and the target sequence is determined to be (or "called") the reference sequence if the likelihood of the reference sequence is significantly higher than the sum of the likelihoods of the 8 sequence variants. This may be carried out as follows:
   (a) The i position of the reference sequence is replaced with each of the 7 possible mutations and the likelihood of each mutation is calculated. The likelihood of the reference sequence itself is also calculated.
   (b) The likelihood for the reference sequence is divided by the sum of the likelihoods of all 8 sequence variants (which includes the reference sequence). If this ratio (reference to sum of mutations) value is greater than Threshold 1, and preferably if the ratio of the second largest likelihood to the third largest likelihood is less than $10^7$, then the i-th position is called the reference sequence.
2) If the ratio obtained in step 1(b) is not greater than Threshold 1, then the largest and second largest likelihoods are compared as follows:
   (a) S1=the largest likelihood (among the likelihoods of the reference sequence and likelihoods of the 8 possible sequence variations). S2=the second largest likelihood among these 10 values. SH12=the likelihood that there is a heterozygote mutation with the two sequences that have the likelihoods S1 and S2.
   (b) If S1/(S1+S2+SH12)>Threshold 2, then the target sequence is called the S1 sequence. (If S1 is not the reference sequence, S1 is considered to be a homozygous mutated sequence.)
   (c) If SH12/(S1+S2+SH12)>Threshold 2, then the target sequence is called a heterozygote of S1 and S2 sequences.
3) If step 2 does not provide enough information to call the target sequence (i.e., neither S1/(S1+S2+SH12) nor SH12/(S1+S2+SH12) is greater than Threshold 2), then the i and i+1 positions (where i+1 is denoted "j") are examined together as follows:
   (a) The i and j positions of the reference sequence are replaced with each of the possible combinations of 8 sequence variants and the likelihood of each double mutation is calculated, as well as the likelihood of the reference sequence.
   (b) The likelihood for the reference sequence is divided by the sum of the likelihoods of all possible double mutations. If this ratio (reference to sum of double mutations) value is greater than Threshold 1, the target sequence at positions i and j is called the reference sequence (because the likelihood of the reference sequence is significantly higher than the sum of the likelihoods of the double mutations).
   (c) If the ratio obtained in step 3(b) is not greater than Threshold 1, then the largest and second largest likelihoods are compared as follows:
      (i) D1=the largest likelihood (among the likelihoods of the reference sequence and likelihoods of all possible double mutations). D2=the second largest likelihood among these values. DH12=the likelihood that there is a heterozygote double mutation with the two sequences that have the likelihoods D1 and D2.
      (ii) If D1/(D1+D2+DH12)>Threshold 2, then the target sequence is called the D1 sequence. (If D1 is not the reference sequence, D1 is considered to be a homozygous mutated sequence.)
   (c) If DH12/(D1+D2+DH12)>Threshold 2, then the target sequence is called a heterozygote of D1 and D2 sequences.
4) If step 3 does not provide enough information to call the target sequence (i.e., neither D1/(D1+D2+DH12) nor DH12/(D1+D2+DH12) is greater than Threshold 2), then the i+2 position may be examined, if desired (and then i+3 and so on), or there may be a "no call" result because of insufficient information to identify clearly the sequence at position i or j.
5) Steps 1-4 may be repeated until the end of the target sequence is reached.

EXAMPLES

Example 1

Computer Simulation Using Pools of 10-Mer Probes in Format 3 SBH

Computer simulations were used to test the described methods. The simulations used Format 3 SBH with 16 pools of 64 5-mers or 32 pools of 32 labeled 5-mers and 16 or 32 full arrays of 1024 fixed 5-mers, respectively. The pools were generated to satisfy various constrains: no reverse complements, no shifts where the first four nucleotides of one probe match the last four nucleotides of the other probe, no pairs of probes in a pool with single nucleotide difference, and minimized number of pairs with only two differences. The simulations tested different randomly generated 300 nucleotide and 1000 nucleotide targets. To simulate actual conditions, some simulations contained randomly generated 30-100% false positive scores.

The simulated raw hybridization data was then used to generate sequence information, according to the following algorithm: For each fixed 5-mer that is positive with a given pool, all possible 10-mer combinations of that fixed 5-mer and all labeled probes from that pool were generated. Each 10-mer so generated was then extended through all 9-nucleotide overlaps with the other generated 10-mers. The 11-mers thus formed were then extended further if any 10-mers matched with the growing end. The design of the experiment was such that false assembles usually grow only for few cycles. Where necessary, some ambiguities in the labeled probes were resolved based on the presence or absence of a corresponding positive results with the fixed probes. In almost all tested cases, all wrong sequences could be eliminated as short, cyclical, or inconsistent with positive/negative results on the fixed probes.

More specifically, two different computer programs were used: BuildFalse (for data sets with no errors or false positives only) and BuildMMult (for data sets with both false positives and false negatives). The code for both programs is found in Appendix 1. The programs were tested with a 300 nucleotide target sequence, r300 (Appendix 2), "probed" with two different sets of pools of 5-mer probes, D16 and DN16 (Appendix 3). The computer programs generated the expected hybridization data, including false positives and false negatives where applicable, then attempted to regenerate the sequence from the simulated hybridization data. Six files starting with r300 and finish with out are simulation results.

All simulations were carried out on the same r300 sequence. Six simulations generated six output files, presented in Appendix 4. The simulation output files are named according to the pattern "r300.x.out", where x describes nature of the simulation: 0.0 represents no errors; 100.0 represents 33% false positives and 0% false negatives; 300.0 represents 100% false positives and 0% false negatives; and 100.15 represents 33% false positives and 5% false negatives. Additionally, the two files with "DN16" in the name used the DN16 set of pools; all others used the D16 set of pools (see Appendix 3). The output files contain (1) a listing of the positive combinations of fixed probes and labeled pools; (2) the stepwise creation of overlaps of increasing lengths; and (3) all solutions of the expected length. In each simulation, one solution was correct and all the other solutions had differences only at the ends, which can be recognized by known primer sequences.

Part (2) of the output files demonstrates the assembly of the sequence by creating all possible 10-mers from all combinations of positive fixed probes with each member of the pool of labeled probes. These 10-mers were then combined into all possible 11-mers by overlapping the positive 10-mers. Next, all the 11-mer blocks were combined over 10 nucleotides, effectively creating 12-mers, in what was equivalent to two steps of adding 10-mers with overlap 9. The process was then repeated with successively longer blocks and overlaps until all 300 nucleotide sequences were generated.

In the case of simulations containing false negatives, 11-mers were also created using 8-nucleotide overlaps in the 10-mer probes in the first step, and then all 11-mers were further combined as in the cases with no false negatives. However, other more efficient options exist for handling false negatives. One option is to build all sequences from 11-mers created by overlaps of 9 or more nucleotides (as in the case with no false negatives), and then to combine these sequences (all or only sufficiently long ones) using end sequences of length 8 and shorter (note that 5% false negatives means an average assembly of 20 nucleotides before a missing probe is hit).

Example 2

Analysis of Single Nucleotide Polymorphisms Using Pools of Probes

Format 3 SBH was carried out using a complete set of 1,048,576 10-mer probes scored for full match hybrids in a DNA sample, by hybridizing and ligating 16 pools of 64 labeled 5-mers on 16 replica arrays containing the full complement of 1024 attached 5-mers. Different DNA targets 100-220 bases in length were successfully sequenced using this procedure.

A 135 bp fragment of the human cytochrome P 450 (CP450) gene with 67.4% G+C content (corresponding to positions 3358-3492 of the sequence deposited under Genbank Accession No. CP450 CYP206) was prepared from genomic DNA using PCR. The CP450 gene has an A/G polymorphism at position 109 of the fragment, and the DNA sample used was heterozygous for this polymorphism, so that the DNA obtained from the sample had both possible sequences. One primer was phosphorylated, to allow degradation of that strand by lambda exonuclease (GIBCO BRL, used according to supplier's instructions) after the PCR product was obtained. DNAse I (GIBCO BRL, used according to supplier's instructions) was used to fragment the resulting single stranded DNA into fragments of about 20-50 bases. A separate hybridization reaction was carried out for each of 16 pools that each contained 64 different probes. For each hybridization reaction, 1 pmol of target DNA, 5 pmols of each of the 64 labeled probes in the pool, and 25 μl of ligation reaction containing 100 units of ligase (New England Biolabs) were added to the hybridization chamber with a complete array of 1024 fixed probes. The hybridization/ligation reactions were carried out for 30 minutes at room temperature in ligase buffer with 10% PEG. The unincorporated labeled probes were removed by a thorough wash with 2×SSPE, 1% sarcosine at 80° C. for one hour. The 16 pools were scored in sixteen hybridization chambers using total of 16 picomols of target (about 100 μl of PCR product). Images were obtained using a General Scanning reader and a hybridization intensity signal was determined for each of the 16,000 spots (each representing a pool of 64 10-mers). Absolute hybridization signals were normalized (by dividing the score by the median score of its unit array) to have the same median value in all array units to avoid experimental differences.

The normalized signals were sorted by descending value, and based on past experience, the top 1200 signals were declared to be putative positive pools. That number of signals represented over nine-fold more positive pools than the expected 126 positive pools and thus included many more false positive pools than expected. However, due to variations in the signal of full match probes and mismatch probes, that number of false positive pools had to be included to assure that about 95% or more of the true positive pools were included in the assembly process. This was especially important because the target DNA contained a heterozygote site, and the 20 10-mers that bound to that heterozygote position would be expected to hybridize to only half of the targets-and thus provide only half of the hybridization signal of other positive probes. The P/T ratio in this case was 1200/16384, about 1/14. About 76,800 10-mers were used in the assembly process.

The algorithms for sequence assembly may be further optimized to properly balance between false positive and false negative scores. Even with significant improvements in discrimination the distributions of hybridization signals from full match probes and from mismatch probes may still overlap to some extent. In the current Format 3 protocol, the average signal ratio of a full match hybrid to a single mismatch hybrid obtained using a short synthetic target is over 20-fold. For the CP450 experiment described in this example, in the top 200 signals there were only 96 out of the predicted 120 full match probes (80%). In order to select 90% of the predicted full match probes (12 additional scores), pooled probes with the top 1000 scores had to be used in the assembly process. In order to select 95% of the predicted full match probes (6 additional scores), pooled probes with the top 1200 scores had to be used in the assembly process.

After the pooled probes with the top 1200 pool hybridization scores were selected as the initial positive probe set, sequence assembly was conducted generally as described above. First, a "clean" positive probe set was selected by overlapping each probe with 8 other probes (4 in each 5' or 3' direction) using the filtering algorithm described above. Only one K-2 overlap (i.e., one missed probe in the 9 probe overlap) was allowed. This optional filtering step was used to simplify full length sequence assembly computations and resulted in an 8.6-fold reduction in the number of probes in the positive probe set.

The "clean" positive probe set was used to assemble overlapping sequences while allowing for 2 consecutive missed probes (i.e. K-2 or K-3 overlaps). The sequence assembly program found 30,313 candidate sequences that were the exact target nucleic acid length of 135 bp and that started and ended with the known primer sequences. The program found 138,698 candidate sequences that were within ±4% of the expected length (ranging from 130-140 bp) and that started and ended with the known primer sequences.

The rescoring procedure described above was used to improve the determination of the correct target nucleic acid sequence. The P values of the probes were determined as described above and the candidate sequences were ranked by summing the rescores for all of the overlapping probes constituting the candidate sequence. After rescoring, the two correct solutions (including the heterozygote site) ranked first and second. The errors in the incorrect sequences were predominantly deletions and exchanges on K-2 overlap sites.

Thus, the use of pools of probes in Format3 SBH demonstrated that the methods of the present invention could be successfully used for de novo sequencing of a difficult 135 bp fragment of CP450 gene characterized by 67.4% C+G content. SBH was able to correctly identify an A/G heterozygote site, even though the 20 "positive" probes that hybridize to this position should have on average a 2-fold lower signal than other positive probes. Using the same approach, sequences of other targets including a 100 bp fragment of human p53 gene (characterized by G+C content of 62.0%) and a 198 bp fragment of the human apolipoprotein B gene (characterized by G+C content of 48.0%) were also correctly determined.

Example 3

Computer Simulation of SBH Using 16,384 Pools of 1024 12-Mers to Assemble 3.2 kb Target Sequences Simulation experiments with pools of 12-mers demonstrated the potential of this SBH approach to determine the sequence of very long target nucleic acid sequences of more than 10 kb in length. (See Table 3 above). Several sequence assembly experiments were conducted with simulated data and pools of 10-mer or 12-mers to measure the minimal redundancy factor for different probe lengths and target nucleic acid lengths.

First, by using 16,384 pools of 64 10-mers, an Fp of ⅕ or less was observed to be sufficient to assemble 800 bases with a success rate similar to that using individual, unpooled probes (in about 90% cases, see Table 1). In addition, there were a large number of false positive pools (pools whose hybridization scores were considered positive despite the fact that they contained no full match probes), e.g., due to random experimental error. Since both true positive and false positive pools are included in the P/T ratio, the high number of false positive pools played a significant role in determining the P/T ratio.

In a second simulation, 16,384 pools of 1024 12-mers were used to test sequence assembly for 3.2 kb sequences that are expected to be uniquely assembled in >=90% cases (see Table 3). The selected parameters define a very restrictive Fp of 3200/16,384=0.196, slightly less than ⅕. One hundred different sequences were tested with the pools and with individual 12-mer probes. Of these 100 test targets, a unique correct sequence was produced in 87 cases, while 10 cases had 2 candidate sequences, 1 case had 3 candidate sequences, 1 case had 4 candidate sequences and 1 case had 12 candidate sequences. When individual, unpooled 12-mer probes were tested against the same 100 test targets, a unique correct sequence was produced in and 91 cases. The use of pools of probes provided less successful results compared to the use of individual probes in only 4 cases (4%). These results indicate that large pools (of 1024 probes) can efficiently determine the sequence of long target nucleic acids with a very low score redundancy (about 5 measurements per base), and demonstrate the computational feasibility of assembling target sequences as long as 3.2 kb.

The present invention is not to be limited in scope by the exemplified embodiments which are intended as illustrations of single aspects of the invention The foregoing specification and accompanying drawings is considered to be sufficient to enable one skilled in the art to broadly practice the invention. Indeed, various modifications of the above-described means for carrying out the invention which are obvious to those skilled in the relevant arts are intended to be within the scope of the following claims. All patents, patents applications, and publications cited herein are hereby incorporated by reference in their entireties for all purposes.

What is claimed is:

1. A set of pools of probes wherein each probe comprises an information region, wherein said set of probes includes a number of individual probes that is sufficient to determine the sequence of an unknown target nucleic acid by overlapping sequences of the information region of two or more of said probes that hybridize to said target nucleic acid, and wherein at least one pool comprises two or more probes having different sequences in the information regions and having the same label or no label, and wherein the set of the pools of probes also satisfies one or more of the following rules describing the information regions of the probes, said rules selected from the group consisting of:

a. a consensus sequence of at least one pool in the set consists only of the letters selected from the group consisting of V, H, D, B, and N;

b. a consensus sequence of probes in each pool in the set comprises more than three different letters selected from the group consisting of A, C, G, T, U, M, R, W, S, Y, K, V, H, D, B, and N;

c. consensus sequences from each informative position of all pools in the set comprise more than eight letters selected from the group consisting of A, C, G, T, U, M, R, W, S, Y, K, V, H, D, B, and N; and d. consensus sequences from each information region of all pools in the set comprise more than five different letters selected from the group consisting of A, C, G, T, U, M, R, W, S, Y, K, V, H, D, B, and N, wherein at least one letter is selected from the group consisting of M, R, W, S, Y, and K.

2. The set of pools of probes of claim 1 wherein said set comprises all possible probes of the same length K, where K is greater than 3.

3. The set of pools of probes of claim 1 wherein each pool comprises more than 16 different probes.

4. The set of pools of probes of claim 3 wherein each pool comprises at least 32 different probes.

5. The set of pools of probes of claim 1 in which the pools are arranged in a spatially-addressable array, and wherein each pool has an address.

6. The set of pools of probes of claim 1 wherein at least two pools are mixed, wherein any two pools that are mixed are associated with different labels, and wherein all probes in a single pool are associated with the same label.

* * * * *

SEQUENCE LISTING

```
<160> NUMBER OF SEQ ID NOS: 71

<210> SEQ ID NO 1
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 1
```

aaaaaaaaaa 10

<210> SEQ ID NO 2
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 2
acacacacac 10

<210> SEQ ID NO 3
<211> LENGTH: 20
<212> TYPE: DNA
<213> ORGANISM: Artificial Sequence
<220> FEATURE:
<223> OTHER INFORMATION: Hypothetical sequence

<400> SEQUENCE: 3
atctgtgtct gaagtagtcc 20

<210> SEQ ID NO 4
<211> LENGTH: 20
<212> TYPE: DNA
<213> ORGANISM: Artificial Sequence
<220> FEATURE:
<223> OTHER INFORMATION: Hypothetical sequence

<400> SEQUENCE: 4
atctctggct gaagtagtcc 20

<210> SEQ ID NO 5
<211> LENGTH: 43
<212> TYPE: DNA
<213> ORGANISM: Artificial Sequence
<220> FEATURE:
<223> OTHER INFORMATION: Hypothetical sequence
<220> FEATURE:
<221> NAME/KEY: misc_feature
<222> LOCATION:
<223> OTHER INFORMATION: b = C or G or T

<400> SEQUENCE: 5
bbbbbbattt cbbbbbgcac tbbbbgtttg bbbacacgbb bbb 43

<210> SEQ ID NO 6
<211> LENGTH: 43
<212> TYPE: DNA
<213> ORGANISM: Artificial Sequence
<220> FEATURE:
<223> OTHER INFORMATION: Hypothetical sequence
<220> FEATURE:
<221> NAME/KEY: misc_feature
<222> LOCATION:
<223> OTHER INFORMATION: b = C or G or T

<400> SEQUENCE: 6
bbbbbbattt gbbbacactb bbbgtttcbb bbbgcacgbb bbb 43

<210> SEQ ID NO 7
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 7
ggtctcccca 10

<210> SEQ ID NO 8
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 8
gtctccccaa 10

<210> SEQ ID NO 9
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 9
tctccccaag 10

<210> SEQ ID NO 10
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 10
ctccccaagg 10

<210> SEQ ID NO 11
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 11
tccccaaggc 10

<210> SEQ ID NO 12
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 12
ccccaaggcg 10

<210> SEQ ID NO 13
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 13
cccaaggcgc 10

<210> SEQ ID NO 14
<211> LENGTH: 10

<212> TYPE: DNA
<213> ORGANISM: Artificial Sequence
<220> FEATURE:
<223> OTHER INFORMATION: Hypothetical sequence

<400> SEQUENCE: 14
ccaaggcgca 10

<210> SEQ ID NO 15
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 15
caaggcgcac 10

<210> SEQ ID NO 16
<211> LENGTH: 30
<212> TYPE: DNA
<213> ORGANISM: Artificial sequence
<220> FEATURE:
<223> OTHER INFORMATION: Hypothetical sequence

<400> SEQUENCE: 16
tgcttgccac aggtctcccc aaggcgcact 30

<210> SEQ ID NO 17
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 17
aggtctcccc 10

<210> SEQ ID NO 18
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 18
ggtctcccca 10

<210> SEQ ID NO 19
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 19
gtctccccaa 10

<210> SEQ ID NO 20
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 20

-continued tctccccaag 10

<210> SEQ ID NO 21
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 21
ctccccaagg 10

<210> SEQ ID NO 22
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 22
tccccaaggc 10

<210> SEQ ID NO 23
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 23
ccccaaggcg 10

<210> SEQ ID NO 24
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 24
cccaaggcgc 10

<210> SEQ ID NO 25
<211> LENGTH: 10
<212> TYPE: DNA
<213> ORGANISM: Artificial Sequences
<220> FEATURE:
<223> OTHER INFORMATION: Hypothetical sequence

<400> SEQUENCE: 25
ccaaggcgca 10

<210> SEQ ID NO 26
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 26
caaggcgcac 10

<210> SEQ ID NO 27
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 27
caggtctccc 10

<210> SEQ ID NO 28
<211> LENGTH: 10
<212> TYPE: DNA
<213> ORGANISM: Artificial Sequences
<220> FEATURE:
<223> OTHER INFORMATION: Hypothetical sequence

<400> SEQUENCE: 28
gcttgccaca 10

<210> SEQ ID NO 29
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 29
cttgccacag 10

<210> SEQ ID NO 30
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 30
ttgccacagg 10

<210> SEQ ID NO 31
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 31
tgccacaggt 10

<210> SEQ ID NO 32
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 32
gccacaggtc 10

<210> SEQ ID NO 33
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 33
ccacaggtgt 10

-continued

<210> SEQ ID NO 34
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 34
cacaggtctc 10

<210> SEQ ID NO 35
<211> LENGTH: 10
<212> TYPE: DNA
<213> ORGANISM: Artificial Sequence
<220> FEATURE:
<223> OTHER INFORMATION: Hypothetical sequence

<400> SEQUENCE: 35
acaggtctcc 10

<210> SEQ ID NO 36
<211> LENGTH: 10
<212> TYPE: DNA
<213> ORGANISM: artificial sequence
<220> FEATURE:
<223> OTHER INFORMATION: Hypothetical sequence

<400> SEQUENCE: 36
agcttgccac 10

<210> SEQ ID NO 37
<211> LENGTH: 10
<212> TYPE: DNA
<213> ORGANISM: artificial sequence
<220> FEATURE:
<223> OTHER INFORMATION: Hypothetical sequence

<400> SEQUENCE: 37
tgcttgccac 10

<210> SEQ ID NO 38
<211> LENGTH: 10
<212> TYPE: DNA
<213> ORGANISM: artificial sequence
<220> FEATURE:
<223> OTHER INFORMATION: Hypothetical sequence

<400> SEQUENCE: 38
cgcttgccac 10

<210> SEQ ID NO 39
<211> LENGTH: 10
<212> TYPE: DNA
<213> ORGANISM: artificial sequence
<220> FEATURE:
<223> OTHER INFORMATION: Hypothetical sequence

<400> SEQUENCE: 39
ggcttgccac 10

<210> SEQ ID NO 40
<211> LENGTH: 10
<212> TYPE: DNA
<213> ORGANISM: artificial sequence
<220> FEATURE:
<223> OTHER INFORMATION: Hypothetical sequence

<400> SEQUENCE: 40
ctcgatccgg 10

<210> SEQ ID NO 41
<211> LENGTH: 300
<212> TYPE: DNA
<213> ORGANISM: Artificial sequence
<220> FEATURE:
<223> OTHER INFORMATION: Hypothetical sequence

<400> SEQUENCE: 41
gtaggggtag acatcgcgta aaaggggcgt acccaggacc ccccttggct caataagtag 60
cgctggggtg ctactacggg tctcgacacg cattcaacta aaagcttcca ttcgcacggg 120
cttatttaac gaaggtcgcg ataaggtgcc gaataggctg cagagcggca gcctgtccag 180
tgaatgctgt gaggcctcca gctgactcat gagagaagcc cagtattcaa actacgattc 240
cactcgacaa tttaggatgt cttcccgaaa gctatcgggt agaatatcag attcgtttaa 300

<210> SEQ ID NO 42
<211> LENGTH: 300
<212> TYPE: DNA
<213> ORGANISM: Artificial sequence
<220> FEATURE:
<223> OTHER INFORMATION: Hypothetical sequence

<400> SEQUENCE: 42
ggtaggggta gacatcgcgt aaaaggggcg tacccaggac cccccttggc tcaataagta 60
gcgctggggt gctactacgg gtctcgacac gcattcaact aaaagcttcc attcgcacgg 120
gcttatttaa cgaaggtcgc gataaggtgc cgaataggct gcagagcggc agcctgtcca 180
gtgaatgctg tgaggcctcc agctgactca tgagagaagc ccagtattca aactacgatt 240
ccactcgaca atttaggatg tcttcccgaa agctatcggg tagaatatca gattcgttta 300

<210> SEQ ID NO 43
<211> LENGTH: 300
<212> TYPE: DNA
<213> ORGANISM: Artificial sequence
<220> FEATURE:
<223> OTHER INFORMATION: Hypothetical sequence

<400> SEQUENCE: 43
ggtaggggta gacatcgcgt aaaaggggcg tacccaggac cccccttggc tcaataagta 60
gcgctggggt gctactacgg gtctcgacac gcattcaact aaaagcttcc attcgcacgg 120
gcttatttaa cgaaggtcgc gataaggtgc cgaataggct gcagagcggc agcctgtcca 180
gtgaatgctg tgaggcctcc agctgactca tgagagaagc ccagtattca aactacgatt 240
ccactcgaca atttaggatg tcttcccgaa agctatcggg tagaatatca gattcgtttg 300

<210> SEQ ID NO 44
<211> LENGTH: 300
<212> TYPE: DNA
<213> ORGANISM: Artificial sequence
<220> FEATURE:
<223> OTHER INFORMATION: Hypothetical sequence

<400> SEQUENCE: 44
ggtaggggta gacatcgcgt aaaaggggcg tacccaggac cccccttggc tcaataagta 60
gcgctggggt gctactacgg gtctcgacac gcattcaact aaaagcttcc attcgcacgg 120

```
gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgtttt    300


<210> SEQ ID NO 45
<211> LENGTH: 300
<212> TYPE: DNA
<213> ORGANISM: Artificial sequence
<220> FEATURE:
<223> OTHER INFORMATION: Hypothetical sequence

<400> SEQUENCE: 45

gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttaa    300


<210> SEQ ID NO 46
<211> LENGTH: 300
<212> TYPE: DNA
<213> ORGANISM: Artificial sequence
<220> FEATURE:
<223> OTHER INFORMATION: Hypothetical sequence

<400> SEQUENCE: 46

gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgttttg    300


<210> SEQ ID NO 47
<211> LENGTH: 300
<212> TYPE: DNA
<213> ORGANISM: Artificial sequence
<220> FEATURE:
<223> OTHER INFORMATION: Hypothetical sequence

<400> SEQUENCE: 47

gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttaa    300


<210> SEQ ID NO 48
<211> LENGTH: 300
<212> TYPE: DNA
<213> ORGANISM: Artificial sequence
<220> FEATURE:
<223> OTHER INFORMATION: Hypothetical sequence

<400> SEQUENCE: 48

ggtaggggta gacatcgcgt aaaaggggcg tacccaggac cccccttggc tcaataagta     60

gcgctggggt gctactacgg gtctcgacac gcattcaact aaaagcttcc attcgcacgg    120
```

```
gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgttta    300


<210> SEQ ID NO 49
<211> LENGTH: 300
<212> TYPE: DNA
<213> ORGANISM: Artificial sequence
<220> FEATURE:
<223> OTHER INFORMATION: Hypothetical sequence

<400> SEQUENCE: 49

gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttaa    300


<210> SEQ ID NO 50
<211> LENGTH: 300
<212> TYPE: DNA
<213> ORGANISM: Artificial sequence
<220> FEATURE:
<223> OTHER INFORMATION: Hypothetical sequence

<400> SEQUENCE: 50

ggtaggggta gacatcgcgt aaaaggggcg tacccaggac cccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgtttt    300


<210> SEQ ID NO 51
<211> LENGTH: 300
<212> TYPE: DNA
<213> ORGANISM: Artificial sequence
<220> FEATURE:
<223> OTHER INFORMATION: Hypothetical sequence

<400> SEQUENCE: 51

gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgttttg    300


<210> SEQ ID NO 52
<211> LENGTH: 300
<212> TYPE: DNA
<213> ORGANISM: Artificial sequence
<220> FEATURE:
<223> OTHER INFORMATION: Hypothetical sequence

<400> SEQUENCE: 52

gggtaggggt agacatcgcg taaaaggggc gtacccagga ccccccttgg ctcaataagt     60
```

-continued agcgctgggg tgctactacg ggtctcgaca cgcattcaac taaaagcttc cattcgcacg 120
ggcttattta acgaaggtcg cgataaggtg ccgaataggc tgcagagcgg cagcctgtcc 180
agtgaatgct gtgaggcctc cagctgactc atgagagaag cccagtattc aaactacgat 240
tccactcgac aatttaggat gtcttcccga aagctatcgg gtagaatatc agattcgttt 300

<210> SEQ ID NO 53
<211> LENGTH: 300
<212> TYPE: DNA
<213> ORGANISM: Artificial sequence
<220> FEATURE:
<223> OTHER INFORMATION: Hypothetical sequence

<400> SEQUENCE: 53
ggtaggggta gacatcgcgt aaaaggggcg tacccaggac ccccccttggc tcaataagta 60 gcgctggggt gctactacgg gtctcgacac gcattcaact aaaagcttcc attcgcacgg 120
gcttatttaa cgaaggtcgc gataaggtgc cgaataggct gcagagcggc agcctgtcca 180
gtgaatgctg tgaggcctcc agctgactca tgagagaagc ccagtattca aactacgatt 240
ccactcgaca atttaggatg tcttcccgaa agctatcggg tagaatatca gattcgtttg 300

<210> SEQ ID NO 54
<211> LENGTH: 300
<212> TYPE: DNA
<213> ORGANISM: Artificial sequence
<220> FEATURE:
<223> OTHER INFORMATION: Hypothetical sequence

<400> SEQUENCE: 54
gggtaggggt agacatcgcg taaaaggggc gtacccagga ccccccttgg ctcaataagt 60
agcgctgggg tgctactacg ggtctcgaca cgcattcaac taaaagcttc cattcgcacg 120
ggcttattta acgaaggtcg cgataaggtg ccgaataggc tgcagagcgg cagcctgtcc 180
agtgaatgct gtgaggcctc cagctgactc atgagagaag cccagtattc aaactacgat 240
tccactcgac aatttaggat gtcttcccga aagctatcgg gtagaatatc agattgtagt 300

<210> SEQ ID NO 55
<211> LENGTH: 300
<212> TYPE: DNA
<213> ORGANISM: Artificial sequence
<220> FEATURE:
<223> OTHER INFORMATION: Hypothetical sequence

<400> SEQUENCE: 55
gtaggggtag acatcgcgta aaaggggcgt acccaggacc ccccttggct caataagtag 60
cgctggggtg ctactacggg tctcgacacg cattcaacta aaagcttcca ttcgcacggg 120
cttatttaac gaaggtcgcg ataaggtgcc gaataggctg cagagcggca gcctgtccag 180
tgaatgctgt gaggcctcca gctgactcat gagagaagcc cagtattcaa actacgattc 240
cactcgacaa tttaggatgt cttcccgaaa gctatcgggt agaatatcag attcgtttaa 300

<210> SEQ ID NO 56
<211> LENGTH: 300
<212> TYPE: DNA
<213> ORGANISM: Artificial sequence
<220> FEATURE:
<223> OTHER INFORMATION: Hypothetical sequence

<400> SEQUENCE: 56
gtaggggtag acatcgcgta aaaggggcgt acccaggacc ccccttggct caataagtag 60

-continued

```
cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcccatgt    300


<210> SEQ ID NO 57
<211> LENGTH: 300
<212> TYPE: DNA
<213> ORGANISM: Artificial sequence
<220> FEATURE:
<223> OTHER INFORMATION: Hypothetical sequence

<400> SEQUENCE: 57

ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcccatg    300


<210> SEQ ID NO 58
<211> LENGTH: 300
<212> TYPE: DNA
<213> ORGANISM: Artificial sequence
<220> FEATURE:
<223> OTHER INFORMATION: Hypothetical sequence

<400> SEQUENCE: 58

gggtaggggt agacatcgcg taaaaggggc gtacccagga ccccccttgg ctcaataagt     60

agcgctgggg tgctactacg ggtctcgaca cgcattcaac taaaagcttc cattcgcacg    120

ggcttattta acgaaggtcg cgataaggtg ccgaataggc tgcagagcgg cagcctgtcc    180

agtgaatgct gtgaggcctc cagctgactc atgagagaag cccagtattc aaactacgat    240

tccactcgac aatttaggat gtcttcccga aagctatcgg gtagaatatc agattcccat    300


<210> SEQ ID NO 59
<211> LENGTH: 300
<212> TYPE: DNA
<213> ORGANISM: Artificial sequence
<220> FEATURE:
<223> OTHER INFORMATION: Hypothetical sequence

<400> SEQUENCE: 59

ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgttta    300


<210> SEQ ID NO 60
<211> LENGTH: 300
<212> TYPE: DNA
<213> ORGANISM: Artificial sequence
<220> FEATURE:
<223> OTHER INFORMATION: Hypothetical sequence

<400> SEQUENCE: 60
```

-continued

```
gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttga    300
```

<210> SEQ ID NO 61
<211> LENGTH: 300
<212> TYPE: DNA
<213> ORGANISM: Artificial sequence
<220> FEATURE:
<223> OTHER INFORMATION: Hypothetical sequence

<400> SEQUENCE: 61

```
gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttaa    300
```

<210> SEQ ID NO 62
<211> LENGTH: 300
<212> TYPE: DNA
<213> ORGANISM: Artificial sequence
<220> FEATURE:
<223> OTHER INFORMATION: Hypothetical sequence

<400> SEQUENCE: 62

```
gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttaa    300
```

<210> SEQ ID NO 63
<211> LENGTH: 300
<212> TYPE: DNA
<213> ORGANISM: Artificial sequence
<220> FEATURE:
<223> OTHER INFORMATION: Hypothetical sequence

<400> SEQUENCE: 63

```
gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcccatgt    300
```

<210> SEQ ID NO 64
<211> LENGTH: 300
<212> TYPE: DNA
<213> ORGANISM: Artificial sequence
<220> FEATURE:
<223> OTHER INFORMATION: Hypothetical sequence

<400> SEQUENCE: 64

```
ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgtttt    300
```

<210> SEQ ID NO 65
<211> LENGTH: 300
<212> TYPE: DNA
<213> ORGANISM: Artificial sequence
<220> FEATURE:
<223> OTHER INFORMATION: Hypothetical sequence

<400> SEQUENCE: 65

```
gtaggggtag acatcgcgta aaaggggcgt acccaggacc ccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgttttg    300
```

<210> SEQ ID NO 66
<211> LENGTH: 300
<212> TYPE: DNA
<213> ORGANISM: Artificial sequence
<220> FEATURE:
<223> OTHER INFORMATION: Hypothetical sequence

<400> SEQUENCE: 66

```
ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcccatg    300
```

<210> SEQ ID NO 67
<211> LENGTH: 300
<212> TYPE: DNA
<213> ORGANISM: Artificial sequence
<220> FEATURE:
<223> OTHER INFORMATION: Hypothetical sequence

<400> SEQUENCE: 67

```
gggtaggggt agacatcgcg taaaaggggc gtacccagga ccccccttgg ctcaataagt     60

agcgctgggg tgctactacg ggtctcgaca cgcattcaac taaaagcttc cattcgcacg    120

ggcttattta acgaaggtcg cgataaggtg ccgaataggc tgcagagcgg cagcctgtcc    180

agtgaatgct gtgaggcctc cagctgactc atgagagaag cccagtattc aaactacgat    240

tccactcgac aatttaggat gtcttcccga aagctatcgg gtagaatatc agattcgttt    300
```

<210> SEQ ID NO 68
<211> LENGTH: 300
<212> TYPE: DNA
<213> ORGANISM: Artificial sequence
<220> FEATURE:
<223> OTHER INFORMATION: Hypothetical sequence -continued

```
<400> SEQUENCE: 68

ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgtttg    300


<210> SEQ ID NO 69
<211> LENGTH: 300
<212> TYPE: DNA
<213> ORGANISM: Artificial sequence
<220> FEATURE:
<223> OTHER INFORMATION: Hypothetical sequence

<400> SEQUENCE: 69

gggtaggggt agacatcgcg taaaaggggc gtacccagga cccccccttgg ctcaataagt     60

agcgctgggg tgctactacg ggtctcgaca cgcattcaac taaaagcttc cattcgcacg    120

ggcttattta acgaaggtcg cgataaggtg ccgaataggc tgcagagcgg cagcctgtcc    180

agtgaatgct gtgaggcctc cagctgactc atgagagaag cccagtattc aaactacgat    240

tccactcgac aatttaggat gtcttcccga aagctatcgg gtagaatatc agattcccat    300


<210> SEQ ID NO 70
<211> LENGTH: 300
<212> TYPE: DNA
<213> ORGANISM: Artificial sequence
<220> FEATURE:
<223> OTHER INFORMATION: Hypothetical sequence

<400> SEQUENCE: 70

ggtaggggta gacatcgcgt aaaaggggcg tacccaggac ccccccttggc tcaataagta     60

gcgctggggt gctactacgg gtctcgacac gcattcaact aaaagcttcc attcgcacgg    120

gcttatttaa cgaaggtcgc gataaggtgc cgaataggct gcagagcggc agcctgtcca    180

gtgaatgctg tgaggcctcc agctgactca tgagagaagc ccagtattca aactacgatt    240

ccactcgaca atttaggatg tcttcccgaa agctatcggg tagaatatca gattcgttta    300


<210> SEQ ID NO 71
<211> LENGTH: 300
<212> TYPE: DNA
<213> ORGANISM: Artificial sequence
<220> FEATURE:
<223> OTHER INFORMATION: Hypothetical sequence

<400> SEQUENCE: 71

gtaggggtag acatcgcgta aaaggggcgt acccaggacc cccccttggct caataagtag     60

cgctggggtg ctactacggg tctcgacacg cattcaacta aaagcttcca ttcgcacggg    120

cttatttaac gaaggtcgcg ataaggtgcc gaataggctg cagagcggca gcctgtccag    180

tgaatgctgt gaggcctcca gctgactcat gagagaagcc cagtattcaa actacgattc    240

cactcgacaa tttaggatgt cttcccgaaa gctatcgggt agaatatcag attcgtttga    300
```